United States Patent
Rowe et al.

(10) Patent No.: US 8,323,335 B2
(45) Date of Patent: Dec. 4, 2012

(54) RETAINING MECHANISMS FOR PROSTHETIC VALVES AND METHODS FOR USING

(75) Inventors: Stanton Rowe, Newport Beach, CA (US); Francesco Maisano, Milan (IT); Oded Meiri, Moshav Ram-On (IL)

(73) Assignee: Edwards Lifesciences Corporation, Irvine, CA (US)

( * ) Notice: Subject to any disclaimer, the term of this patent is extended or adjusted under 35 U.S.C. 154(b) by 575 days.

(21) Appl. No.: 12/368,891

(22) Filed: Feb. 10, 2009

(65) Prior Publication Data

US 2009/0319037 A1   Dec. 24, 2009

Related U.S. Application Data

(60) Provisional application No. 61/074,597, filed on Jun. 20, 2008, provisional application No. 61/088,947, filed on Aug. 14, 2008.

(51) Int. Cl.
A61F 2/24 (2006.01)
(52) U.S. Cl. ..................................................... 623/2.11
(58) Field of Classification Search .................. 623/2.1, 623/2.11; 128/898
See application file for complete search history.

(56) References Cited

U.S. PATENT DOCUMENTS

| | | |
|---|---|---|
| 3,409,013 A | 11/1968 | Berry |
| 3,467,101 A | 9/1969 | Fogarty et al. |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |

(Continued)

FOREIGN PATENT DOCUMENTS

DE       2246526       3/1973

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

(Continued)

Primary Examiner — Melanie Tyson
(74) Attorney, Agent, or Firm — David L. Hauser

(57) ABSTRACT

Disclosed herein are representative embodiments of methods, apparatus, and systems used to deliver a prosthetic heart valve to a deficient valve. In one embodiment, for instance, a support stent is delivered to a position on the surface of the outflow side of a native heart valve of a patient, the support stent defining a support-stent interior. An expandable prosthetic heart valve is delivered into the native heart valve from the inflow side of the native heart valve and into the support-stent interior. The expandable prosthetic heart valve is expanded while the expandable prosthetic valve is in the support-stent interior and while the support stent is at the position on the surface of the outflow side of the heart valve, thereby causing one or more of the native leaflets of the native heart valve to be frictionally secured between the support stent and the expanded prosthetic heart valve.

11 Claims, 20 Drawing Sheets

U.S. PATENT DOCUMENTS

| | | | |
|---|---|---|---|
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Sammuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,383,905 A | 1/1995 | Golds et al. | |
| 5,397,351 A | 3/1995 | Pavcnik et al. | |
| 5,411,055 A | 5/1995 | Kane et al. | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely | |
| 5,554,185 A | 9/1996 | Block et al. | |
| 5,571,175 A | 11/1996 | Vanney et al. | |
| 5,591,185 A | 1/1997 | Kilmer et al. | |
| 5,607,464 A | 3/1997 | Trescony et al. | |
| 5,609,626 A | 3/1997 | Quijano et al. | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian | |
| 6,302,906 B1 | 10/2001 | Goecoechea et al. | |
| 6,350,277 B1 | 2/2002 | Kocur | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle | |
| 6,482,228 B1 | 11/2002 | Norred | |
| 6,488,704 B1 | 12/2002 | Connelly et al. | |
| 6,569,196 B1 | 5/2003 | Vesely et al. | |
| 6,605,112 B1 | 8/2003 | Moll | |
| 6,730,118 B2 | 5/2004 | Spenser et al. | |
| 6,733,525 B2 | 5/2004 | Yang et al. | |
| 6,752,813 B2 | 6/2004 | Goldfarb et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,201,772 B2 | 4/2007 | Schwammenthal et al. | |
| 7,276,078 B2 | 10/2007 | Spenser et al. | |
| 7,276,084 B2 | 10/2007 | Yang et al. | |
| 7,374,571 B2 | 5/2008 | Pease et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| 7,462,191 B2 | 12/2008 | Spenser et al. | |
| 7,621,948 B2 | 11/2009 | Herrmann et al. | |
| 2001/0021872 A1 | 9/2001 | Bailey et al. | |
| 2002/0032481 A1 | 3/2002 | Gabbay | |
| 2002/0173842 A1 | 11/2002 | Buchanan | |
| 2003/0036791 A1 | 2/2003 | Philipp et al. | |
| 2003/0050694 A1 | 3/2003 | Yang et al. | |
| 2003/0100939 A1 | 5/2003 | Yodfat et al. | |
| 2003/0212454 A1 | 11/2003 | Scott et al. | |
| 2004/0039436 A1 | 2/2004 | Spenser et al. | |
| 2004/0127982 A1 | 7/2004 | Machold | |
| 2004/0186565 A1 | 9/2004 | Schreck | |
| 2004/0243230 A1 | 12/2004 | Navia et al. | |
| 2004/0260389 A1 | 12/2004 | Case et al. | |
| 2005/0137688 A1 | 6/2005 | Salahieh et al. | |
| 2005/0137691 A1* | 6/2005 | Salahieh et al. | 623/2.11 |
| 2005/0137698 A1 | 6/2005 | Salahich et al. | |
| 2005/0197696 A1 | 9/2005 | Gomez Duran | |
| 2005/0234546 A1 | 10/2005 | Nugent et al. | |
| 2006/0025857 A1 | 2/2006 | Bergheim et al. | |
| 2006/0149350 A1 | 7/2006 | Patel et al. | |
| 2006/0195134 A1 | 8/2006 | Crittenden | |
| 2006/0229719 A1 | 10/2006 | Marquez et al. | |
| 2006/0259137 A1 | 11/2006 | Artof et al. | |
| 2007/0005131 A1 | 1/2007 | Taylor | |
| 2007/0016286 A1 | 1/2007 | Herrmann et al. | |
| 2007/0100439 A1 | 5/2007 | Cangialosi et al. | |
| 2007/0112422 A1 | 5/2007 | Dehdashtian | |
| 2007/0142906 A1 | 6/2007 | Figulla et al. | |
| 2007/0213813 A1 | 9/2007 | Von Segesser et al. | |
| 2008/0065011 A1 | 3/2008 | Marchand et al. | |
| 2008/0071361 A1* | 3/2008 | Tuval et al. | 623/2.1 |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |

| | | | |
|---|---|---|---|
| 2008/0071369 | A1 | 3/2008 | Tuval et al. |
| 2008/0154355 | A1 | 6/2008 | Benichou et al. |
| 2008/0208328 | A1 | 8/2008 | Antocci et al. |
| 2008/0208332 | A1 | 8/2008 | Lamphere et al. |
| 2008/0221672 | A1 | 9/2008 | Lamphere et al. |
| 2008/0255660 | A1 | 10/2008 | Guyenot et al. |
| 2008/0255661 | A1 | 10/2008 | Straubinger et al. |
| 2009/0054968 | A1 | 2/2009 | Bonhoeffer et al. |
| 2009/0062908 | A1 | 3/2009 | Bonhoeffer et al. |
| 2009/0171432 | A1 | 7/2009 | Von Segesser et al. |
| 2009/0171447 | A1 | 7/2009 | Von Segesser et al. |
| 2009/0222076 | A1 | 9/2009 | Figulla et al. |
| 2009/0287299 | A1 | 11/2009 | Tabor et al. |
| 2010/0016958 | A1 | 1/2010 | St. Goar et al. |

FOREIGN PATENT DOCUMENTS

| | | |
|---|---|---|
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1570809 | 9/2005 |
| EP | 1629795 | 3/2006 |
| FR | 2788217 | 7/2007 |
| GB | 2056023 | 3/1981 |
| SU | 1271508 | 11/1986 |
| WO | 91/17720 | 11/1991 |
| WO | 92/17118 | 10/1992 |
| WO | 93/01768 | 2/1993 |
| WO | 97/24080 | 7/1997 |
| WO | 98/29057 | 7/1998 |
| WO | 99/33414 | 7/1999 |
| WO | 99/40964 | 8/1999 |
| WO | 99/47075 | 9/1999 |
| WO | 00/18333 | 4/2000 |
| WO | 00/41652 | 7/2000 |
| WO | 00/47139 | 8/2000 |
| WO | 01/35878 | 5/2001 |
| WO | 01/49213 | 7/2001 |
| WO | 01/54624 | 8/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/047468 | 6/2003 |
| WO | 2005/087140 | 9/2005 |
| WO | 2006/014233 | 2/2006 |
| WO | 2006/034008 | 3/2006 |
| WO | 2008/005405 | 1/2008 |
| WO | 2008/035337 | 3/2008 |
| WO | 2008/147964 | 12/2008 |
| WO | 2008/150529 | 12/2008 |
| WO | WO2009024859 | 6/2009 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Urban, M.D., Philip, "Coronary Artery Stenting," Editions Médecine et Hygiène, Genève, 1991, pp. 5-47.

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Al Zaibag, Muayed, et al., "Percutaneous Balloon Valvotomy in Tricuspid Stenosis," British Heart Journal, Jan. 1987, vol. 57, No. 1, pp. 51-53.

Lawrence, Jr., M.D., David D., "Percutaneous Endovascular Graft: Experimental Evaluation," Radiology 1897; 163: 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, 2$^{nd}$ Edition, W.B. Saunders Company, Philadelphia, PA, © 1994, 1990, pp. 803-815.

Rösch, M.D., Josef, "The Birth, Early Years and Future of Interventional Radiology," J Vasc Interv Radiol 2003; 14:841-853.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Ross, F.R.C.S., D.N., "Aortic Valve Surgery," Guy's Hospital, London, pp. 192-197, approximately 1968.

Rashkind, M.D., William J., "Creationof an Atrial Septal Defect Withoput Thoracotomy," the Journal of the American Medical Association, vol. 196, No. 11, Jun. 13, 1966, pp. 173-174.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Curriculum Vitae of Robert A. Ersek, M.D., FACS, Jul. 10, 2009, http://www.ersek.com/rae-cv.htm.

Partial Search Report from corresponding case No. PCT/US2009/048035 dated Feb. 26, 2010.

* cited by examiner

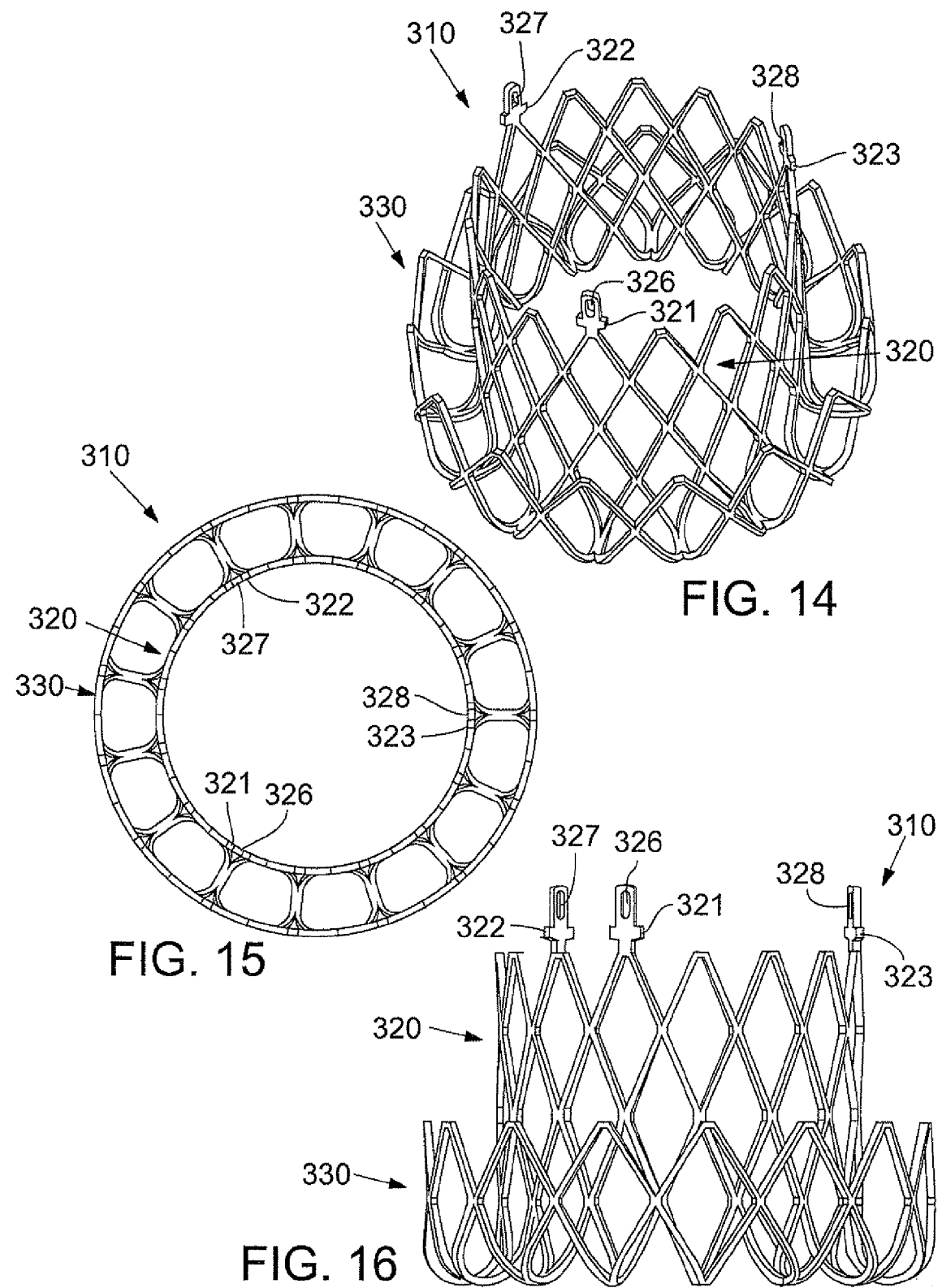

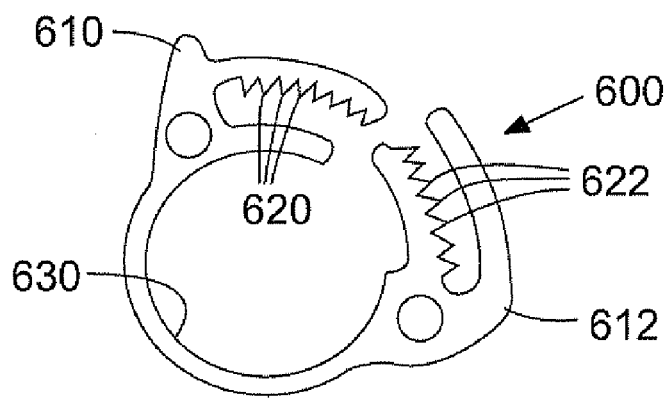
FIG. 29
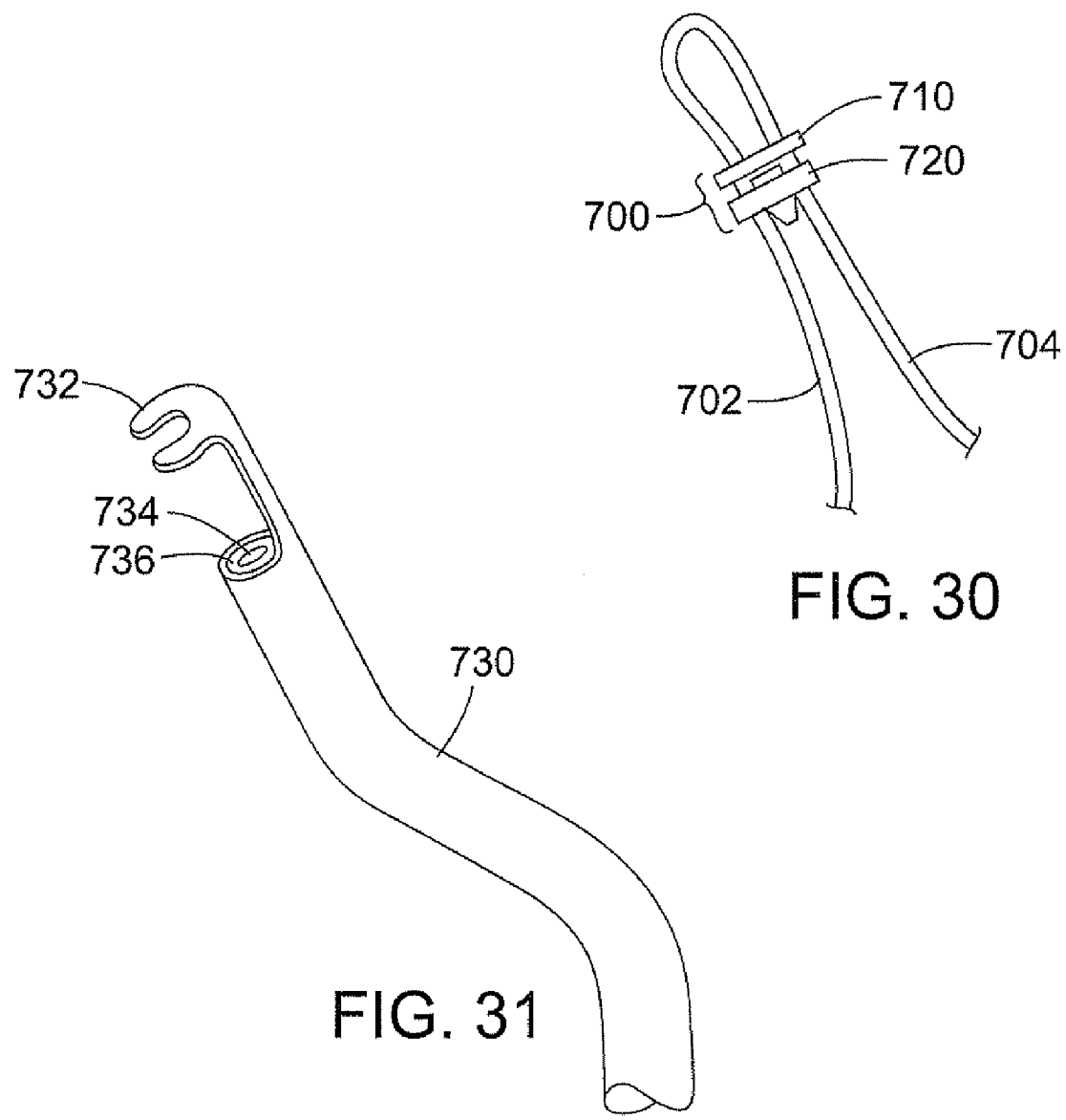
FIG. 30
FIG. 31

RETAINING MECHANISMS FOR PROSTHETIC VALVES AND METHODS FOR USING

CROSS-REFERENCE TO RELATED APPLICATIONS

This application claims the benefit of U.S. Provisional Application No. 61/074,597 filed Jun. 20, 2008, and U.S. Provisional Application No. 61/088,947 filed Aug. 14, 2008, both of which are hereby incorporated herein by reference.

FIELD

This application relates to methods, systems, and apparatus for safely replacing native heart valves with prosthetic heart valves.

BACKGROUND

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Balloon-expandable valves are commonly used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue. There are several heart conditions, however, that do not involve hardened valve leaflets but which are still desirably treated by valve replacement. For example, aortic insufficiency (or aortic regurgitation) occurs when an aortic valve does not close properly, allowing blood to flow back into the left ventricle. One cause for aortic insufficiency is a dilated aortic annulus, which prevents the aortic valve from closing tightly. In such cases, the leaflets are usually too soft to provide sufficient support for a balloon-expandable prosthetic valve. Additionally, the diameter of the aortic annulus may continue to vary over time, making it dangerous to install a prosthetic valve that is not reliably secured in the valve annulus. Mitral insufficiency (or mitral regurgitation) involves these same conditions but affects the mitral valve.

Self-expanding prosthetic valves are sometimes used for replacing defective native valves with noncalcified leaflets. Self-expanding prosthetic valves, however, suffer from a number of significant drawbacks. For example, once a self-expanding prosthetic valve is placed within the patient's defective heart valve (e.g., the aorta or mitral valve), it continues to exert an outward force on the valve annulus. This continuous outward pressure can cause the valve annulus to dilate further, exacerbating the condition the valve was intended to treat. Additionally, when implanting a self-expanding valve, the outward biasing force of the valve's frame tends to cause the valve to be ejected very quickly from the distal end of a delivery sheath. This makes delivery of the valve very difficult and dangerous to the patient.

The size of the prosthetic valve to be implanted into a patient can also be problematic when treating aortic or mitral insufficiency. Specifically, the size of a prosthetic valve used to treat aortic or mitral insufficiency is typically larger than a prosthetic valve used to treat aortic or mitral stenosis. This larger valve size makes the delivery procedure much more difficult and dangerous to the patient.

Accordingly, there exists a need for improved methods, systems, and apparatus for delivering expandable prosthetic heart valves (e.g., balloon-expandable prosthetic valves). Embodiments of the methods, systems, and apparatus desirably can be used to replace native heart valves that do not have calcified leaflets (e.g., aortic valves suffering from aortic insufficiency). Furthermore, embodiments of the methods, systems, and apparatus desirably enable precise and controlled delivery of the prosthetic valves.

SUMMARY

Disclosed below are representative embodiments of methods, systems, and apparatus used to replace deficient native heart valves with prosthetic heart valves. Embodiments of the disclosed methods, systems, and apparatus can be used, for example, to replace an aortic valve suffering from aortic insufficiency or a mitral valve suffering from mitral insufficiency. These embodiments are not limiting, however, as the disclosed methods, systems, and apparatus can be more generally applied to replace any heart valve.

In certain embodiments, for example, a support structure is delivered to a position on or adjacent to the surface of the outflow side of a native heart valve of a patient, the support structure defining a support-structure interior. An expandable prosthetic heart valve is delivered into the native heart valve and into the support-structure interior. The expandable prosthetic heart valve can be expanded while the expandable prosthetic heart valve is in the support-structure interior and while the support structure is at the position on or adjacent to the surface of the outflow side of the native heart valve, thereby causing one or more native leaflets of the native heart valve to be frictionally secured between the support structure and the expanded prosthetic heart valve. The expandable prosthetic heart valve can be delivered from the inflow or the outflow side of the native heart valve. In certain embodiments, the native heart valve is an aortic valve, and the act of delivering the expandable prosthetic heart valve comprises delivering the prosthetic heart valve through the left ventricle of the patient's heart. In other embodiments, the native heart valve is an aortic valve, and the act of delivering the expandable prosthetic heart valve comprises delivering the prosthetic heart valve through the patient's aorta. In particular embodiments, the native heart valve is an aortic valve, the support structure is a support stent, and the act of delivering the support structure comprises advancing a first catheter through the aortic arch of the patient so that a distal end of the first catheter is near the aortic valve of the patient (the first catheter at least partially enclosing a stent-delivery catheter, an inner catheter, and the support stent in a compressed state) and advancing the stent-delivery catheter and the inner catheter through the first catheter, thereby causing the support stent to be deployed from the distal end of the first catheter and to expand into a decompressed state. In other particular embodiments, the native heart valve is a mitral valve, the support structure is a support band, and the act of delivering the support structure comprises advancing a first loop delivery catheter into the left ventricle of the patient so that a first distal end of the first loop delivery catheter extends around a first portion of the chordae tendineae, advancing a second loop delivery catheter into the left ventricle of the patient so that a second distal end of the second loop delivery catheter extends around a second portion of the chordae tendineae and so that the second distal end of the second loop delivery is adjacent to the first distal end of the first loop delivery catheter, advancing a support band material through an interior of the first loop delivery catheter and an interior of the second loop delivery catheter, attaching a locking member to portions of the support band material, and advancing the locking member along the portions of the support band material and into the left ventricle of the patient, thereby forming the support band around the chordae tendineae. In certain embodiments, the act of delivering the support structure comprises guiding the support structure to the position on or adjacent to the surface of the outflow side of the native heart valve and into a desired orientation, wherein the desired orientation aligns peaks of the support structure with either the tips or the commissures of the one or more native leaflets. In further embodiments, the support structure is disconnected from at least a delivery catheter once the one or more native leaflets of the native heart valve are frictionally secured between the support structure and the expanded prosthetic heart valve. The disconnecting can be performed by retracting an inner catheter relative to a stent-delivery catheter, thereby retracting inner prongs coupled to the inner catheter from corresponding apertures in retaining arms of the support stent. Alternatively, the disconnecting can be performed by cutting through material used to form the support structure, thereby releasing the support structure from a catheter. In certain embodiments, the act of expanding the expandable prosthetic heart valve comprises inflating a balloon of a balloon catheter, the expandable prosthetic heart valve being disposed around the balloon of the balloon catheter.

In other exemplary methods disclosed herein, a guide catheter is advanced through the aortic arch of a patient so that a distal end of the guide catheter is near the aortic valve of the patient. In these embodiments, the guide catheter at least partially encloses a stent-delivery catheter and a compressed support stent releasably connected to the stent-delivery catheter. The stent-delivery catheter is advanced through the guide catheter, thereby causing the support stent to be deployed from the distal end of the guide catheter and to become uncompressed. The uncompressed support stent is positioned adjacent to or on a surface of the aortic side of the aortic valve such that the leaflets of the aortic valve are circumscribed by the uncompressed support stent. The uncompressed support stent can then be disconnected from the stent-delivery catheter. In certain embodiments, to disconnect the support stent from the stent-delivery catheter, an inner catheter positioned in the interior of the stent-delivery catheter can be retracted, causing an inner prong attached to the inner catheter to withdraw from an aperture associated with the support stent, and/or at least one prong attached to the stent-delivery catheter can be disconnected from the support stent.

Other exemplary embodiments disclosed herein include apparatus for securing a prosthetic valve to a native heart valve. For example, certain embodiments comprise a support stent having an annular body that defines one or more peaks and one or more valleys along its circumference. The support stent can be radially compressible and self expandable. The support stent can be sized such that it can be positioned within the aorta of a patient at a location adjacent to the aortic valve and thereby circumscribe the aortic valve. The support stent can further comprise at least one retaining arm comprises an aperture at or near a respective one of the peaks. In particular embodiments, the support stent is formed from a single annular member. In some embodiments, the support stent consists of three peaks and three valleys. The shape formed by the three peaks and the three valleys can approximate the shape of the leaflets of the aortic valve when the aortic valve is fully opened. In certain embodiments, a projection of the annular body onto a first plane is ring shaped or starfish shaped, and the annular body defines the one or more peaks and the one or more valleys in a direction perpendicular to the first plane. For example, the annular body can be sinusoidal or saw-tooth shaped along its circumference. Certain embodiments further comprise a stent delivery catheter having an outer fork that includes one or more outer prongs. At least one of the outer prongs can comprise an aperture that is sized to receive at least a portion of one of the retaining arms of the support stent. An inner catheter can be positioned in an interior of the stent-delivery catheter and have an inner fork. The inner fork can comprise one or more inner prongs, and at least one of the inner prongs can be insertable through the aperture of the one of the retaining arms when the one of the retaining arms has been at least partially inserted through the aperture of a respective one of the outer prongs.

Other exemplary embodiments disclosed herein are systems for delivering a support frame for securing a prosthetic valve in a patient's native heart valve. Exemplary embodiments of the system comprise a guide catheter, a frame-delivery catheter positioned in the interior of the guide catheter, an inner catheter positioned in the interior of the frame-delivery catheter, and an expandable support frame positioned in the interior of the guide catheter in a radially compressed state. A distal end of the frame-delivery catheter can have an outer fork portion that comprises a plurality of flexible outer prongs. A distal end of the inner catheter can have an inner fork portion that comprises a plurality of flexible inner prongs. The expandable support frame can comprise a plurality of retaining arms, which can be releasably connected to corresponding ones of the outer prongs of the outer fork portion and corresponding ones of the inner prongs of the inner fork portion. The expandable support frame can be generally annular and comprise shaped portions configured to frictionally secure native leaflets of a patient's heart valve against an exterior surface of a prosthetic valve when the patient's heart valve has been replaced by the prosthetic valve. Alternatively, the expandable support frame can comprise a main body and a U-shaped lip that surrounds a bottom region of the support frame, the U-shaped lip having a diameter that is greater than a diameter of the main body. In particular embodiments, the guide catheter, frame-delivery catheter, and the inner catheter are axially slidable relative to one another. In some embodiments, the retaining arms of the expandable support frame comprise respective retaining arm apertures through which the corresponding ones of the inner prongs are inserted. The corresponding ones of the outer prongs can comprise, for example, respective outer prong apertures through which the respective retaining arms are inserted. In certain embodiments, the corresponding ones of the outer prongs and the corresponding ones of the inner prongs of the inner fork portion are configured such that relative retraction of either the corresponding ones of the inner prongs or the corresponding ones of the outer prongs causes release of the respective retaining arms.

Another disclosed embodiment is an apparatus comprising a support stent having an annular main body portion and a generally U-shaped rim portion at one end of the main body portion. The support stent of this embodiment is radially compressible into a compressed state and self expandable into an uncompressed state. Furthermore, the rim portion has a diameter that is greater than a diameter of the annular main body portion and that is sized so that an outer perimeter of the rim portion will engage the walls surrounding the aortic valve of a patient when the support stent is positioned within the aorta of the patient at a location adjacent to the aortic valve. In some embodiments, the support stent is made of a shape-memory alloy. In certain embodiments, the annular main body portion is sinusoidal or saw-tooth shaped along its circumference. In some embodiments, the rim portion is located around a bottom region of the main body portion. In certain embodiments, the support stent is made of multiple elements forming a criss-cross pattern. In particular embodiments, the apparatus further comprises at least one retaining arm at or near a top region of the main body portion.

In another disclosed embodiment, a distal end of a first delivery catheter is advanced into the left ventricle of a patient so that a distal portion of the first delivery catheter substantially circumscribes a first half of the patient's chordae tendineae. A distal end of a second delivery catheter is advanced into the left ventricle of the patient so that a distal portion of the second delivery catheter substantially circumscribes a second half of the patient's chordae tendineae and so that a distal end of the second delivery catheter contacts a distal end of the first delivery catheter, thereby forming a delivery catheter junction. A support band material is advanced through one of the first delivery catheter or the second delivery catheter, across the delivery catheter junction, and into the other one of the first delivery catheter or the second delivery catheter. The first delivery catheter and the second delivery catheter are retracted from the left ventricle of the patient. In certain embodiments, the distal end of the first delivery catheter and the distal end of the second delivery catheter are advanced through a puncture in the left ventricle. In other embodiments, the distal end of the first delivery catheter and the distal end of the second delivery catheter are advanced through the aorta of the patient. In some embodiments, the distal end of the first delivery catheter magnetically engages the distal end of the second delivery catheter. In some embodiments, a first steerable sheath and a second steerable sheath are advanced into the left ventricle. In these embodiments, the act of advancing the distal end of the first delivery catheter into the left ventricle comprises advancing the distal end of the first delivery catheter through an interior of the first steerable sheath, and the act of advancing the distal end of the second delivery catheter into the left ventricle comprises advancing the distal end of the second delivery catheter through an interior of the second steerable sheath. In certain embodiments, an introducer sheath is advanced into the left ventricle through a puncture in the left ventricle. In these embodiments, the act of advancing the first steerable sheath and the second steerable sheath into the left ventricle comprises advancing the first steerable sheath and the second steerable sheath through the introducer sheath. In some embodiments, a locking member is attached to portions of the support band material and advanced over the portions of the support band material, thereby adjusting a diameter of a loop formed by the support band material and the locking member and surrounding the chordae tendineae. The act of advancing the locking member over the portions of the support band material can be performed using a pusher tube. In some embodiments, the loop formed by the support band material and the locking member can be positioned around the outflow side of the mitral valve. An expandable prosthetic heart valve can be advanced into the mitral valve and the interior of the loop formed by the support band material and the locking member while the prosthetic heart valve is in a compressed state. The expandable prosthetic heart valve can be expanded into an uncompressed state, thereby causing one or more native leaflets of the mitral valve to be frictionally secured between the loop and the expandable prosthetic heart valve. Portions of the support band material that do not form part of the loop can be severed, thereby releasing the loop.

In another disclosed embodiment, a partial loop is formed around the chordae tendineae of a patient's heart with a cord of biocompatible material. A locking member is attached to portions of the cord of biocompatible material. The locking member is advanced toward the chordae tendineae along the portions of the cord of biocompatible material, thereby decreasing a diameter of a loop formed by the cord of biocompatible material and the locking member. In certain embodiments, an expandable prosthetic heart valve is positioned into the interior of the patient's mitral valve, the loop formed by the cord of biocompatible material and the locking member is positioned around an outflow side of the patient's mitral valve so that the native leaflets of the mitral valve open into the interior of the loop, and the expandable prosthetic heart valve is expanded, thereby causing an exterior surface of the expandable prosthetic heart valve to urge the native leaflets of the mitral valve against an interior surface of the loop and to frictionally secure the expandable prosthetic heart valve to the native leaflets of the mitral valve. In some embodiments, portions of the cord of biocompatible material are cut in order to release the loop formed by the cord of biocompatible material and the locking member. In certain embodiments, an expandable prosthetic heart valve is advanced into the interior of the patient's mitral valve and expanded. The exterior of the expandable prosthetic heart valve can comprise one or more fastening mechanisms configured to engage the native leaflets of the mitral valve and at least temporarily secure the expandable prosthetic heart to the native leaflets. In certain implementations of these embodiments, the loop formed by the cord of biocompatible material and the locking member is positioned around an outflow side of the patient's mitral valve so that the loop circumscribes the native leaflets of the mitral valve and the expanded prosthetic heart valve. In these embodiments, the act of advancing the locking member can decrease the diameter of the loop formed by the cord of biocompatible material and the locking member to a diameter that causes the expanded prosthetic heart valve to be frictionally secured to the native leaflets of the mitral valve. In certain particular embodiments, the locking member is locked at a desired position along the portions of the support band material, thereby forming a support band having a substantially fixed diameter. In some embodiments, the locking member can be unlocked, and the location of the locking member adjusted along the portions of the support band material. In certain embodiments, the act of forming the partial loop around the chordae tendineae of the patient's heart is performed using one or more delivery catheters inserted through the aortic arch of the patient. In other embodiments, the act of forming the partial loop around the chordae tendineae of the patient's heart is performed using one or more delivery catheters inserted through a puncture in the left ventricle of the patient.

Another disclosed embodiment is a system that comprises a first delivery catheter having a first distal end region and a first distal end, a second delivery catheter having a second distal end region and a second distal end, and an introducer sheath defining an interior that is configured to receive the first delivery catheter and the second delivery catheter. In these embodiments, the first distal end region is steerable into a first semi-circular shape, the second distal end region is steerable into a second semi-circular shape, the first distal end has a first magnetic polarity, and the second distal end has a second magnetic polarity opposite the first magnetic polarity. In certain embodiments, the introducer sheath is rigid and is sized for insertion through a puncture in the left ventricle of a patient. In other embodiments, the introducer sheath is bendable and is sized for insertion into the aortic arch of a patient. In some embodiments, the system further comprises a first catheter delivery sheath and a second catheter delivery sheath. In these embodiments, the first catheter delivery sheath defines a first interior configured to receive the first delivery catheter and has a first distal sheath region that naturally assumes a first arced shape. Further, the second catheter delivery sheath defines a second interior configured to receive the second delivery catheter and has a second distal sheath region that naturally assumes a second arced shape. In these embodiments, the interior of the introducer sheath is further configured to receive the first catheter delivery sheath, the second catheter delivery sheath, the first delivery catheter, and the second delivery catheter. In certain embodiments, the first catheter delivery sheath and the second catheter delivery sheath are manufactured at least in part from a shape-memory alloy.

Another disclosed embodiment is a system comprising a pusher tube defining a first pusher tube lumen and a second pusher tube lumen and a locking member defining a first locking member lumen and a second locking member lumen. In these embodiments, the first and second pusher tube lumens are sized to receive respective portions of a cord of material, and the first and second locking member lumens are also sized to receive the respective portions of the cord and are further configured to allow movement of the locking member in a first direction along the respective portions of the cord when pushed by the pusher tube but prevent movement of the locking member in a second direction opposite the first direction along the respective portions of the cord. In certain embodiments, the pusher tube further comprises a rotatable cutting element located at a distal end of the pusher tube, the rotatable cutting element being controllable from a proximal region of the pusher tube. In some embodiments, the first locking member lumen and the second locking member lumen each comprise one or more angled collars or teeth. In certain embodiments, the system further comprises an introducer sheath having an introducer sheath interior through which the pusher tube and the locking member are advanceable. In some embodiments, the system further comprises a prosthetic-heart-valve-delivery catheter. In these embodiments, the introducer sheath interior is further configured to simultaneously receive the pusher tube and the prosthetic-heart-valve-delivery catheter.

Another disclosed embodiment is a system comprising a locking member configured to receive two portions of a cord of biocompatible material and to secure the two portions in a desired position relative to one another, an adjustment tool configured to position the locking member into the desired position and to engage a locking mechanism in the locking member that secures the locking member to the two portions at the desired position, a balloon catheter on which an expandable prosthetic heart valve is disposed, and an introducer sheath defining an interior in which the adjustment tool and the balloon catheter can be simultaneously located. In certain embodiments, the adjustment tool is further configured to disengage the locking mechanism in the locking member, thereby unlocking the locking member from the two portions of the cord. In particular embodiments, the locking member comprises a pin member and a ring member. The pin member can have a first end, a second end, and openings for receiving the two portions of the cord, and the ring member can have openings for receiving the two portions of the cord and be configured to receive at least a portion of the first end of the pin member. In some embodiments, the adjustment tool comprises a fork member positioned at a distal end of the adjustment tool, an inner push member, and an outer push member. In these embodiments, the inner push member can be contained within a lumen of the adjustment tool and the outer push member can have a greater diameter than the inner push member and surround at least a portion of the inner push member.

Another disclosed embodiment comprises a support band having an annular body that defines a support band interior. The support band of this embodiment is formed from a biocompatible material having a first end that is secured to an opposite second end via a locking mechanism. The support band of this embodiment is sized such that it can be positioned adjacent to the outflow side of the mitral valve of a patient and thereby circumscribe the native leaflets of the mitral valve. Moreover, the support band interior has a fixed diameter when the first end is secured to the second end such that when an expandable prosthetic heart valve is expanded within the mitral valve and within the support band interior, the native leaflets of the mitral valve become pinched between the expandable prosthetic heart valve and the support band, thereby frictionally securing the expandable prosthetic heart valve to the mitral valve. In certain embodiments, the first end of the support band has a larger diameter than the second end, and the first end of the support band defines an interior into which the second end can be inserted and secured by the locking mechanism. In some embodiments, the locking mechanism comprises a snap-fit connection formed between the first end and the second end of the support band. In certain embodiments, the locking mechanism comprises a locking member having a first lumen configured to receive the first end of the support band and a second lumen configured to receive the second end of the support band, the first lumen and the second lumen each comprising one or more angled teeth or collars that allow movement of the locking mechanism along the support band in only a single direction. In some embodiments, the locking mechanism comprises a multi-element mechanism that can be selectively locked to and unlocked from the first end and the second end of the support band. In certain embodiments, one or more clamps are positioned on the support band.

In another disclosed embodiment, a prosthetic heart valve is delivered into an interior of a native heart valve and expanded. A support band is delivered to a position on or adjacent to the surface of the outflow side of the native heart valve such that an interior of the support band surrounds at least a portion of the prosthetic heart valve and at least a portion of one or more native leaflets of the native heart valve. The diameter of the support band is adjusted until the one or more native leaflets of the native heart valve are frictionally secured between the support band and the prosthetic heart valve. The prosthetic heart valve can be an expandable prosthetic heart valve and expanded once it is delivered into the interior of the native heart valve. The support band can be formed from a shape-memory metal or cord of support band material and an adjustable locking member through which portions of the cord extend. During delivery of the support band, the support band can be disconnected from at least a delivery catheter once the one or more native leaflets of the native heart valve are frictionally secured between the support band and the prosthetic heart valve (e.g., by cutting through material used to form the support band).

The foregoing and other objects, features, and advantages of the disclosed technology will become more apparent from the following detailed description, which proceeds with reference to the accompanying figures.

BRIEF DESCRIPTION OF THE DRAWINGS

FIG. 3 shows the delivery system before the support structure is deployed, and FIG. 4 shows the delivery system after the support structure is deployed.

FIG. 14 is a perspective view of another exemplary embodiment of a support structure according to the disclosed technology.

FIG. 15 is a top view of the support structure embodiment shown in FIG. 14

FIG. 16 is a side view of the support structure embodiment shown in FIG. 14.

In FIGS. 19-27, the support band is deployed using a transapical approach.

FIG. 29 is a top view of an exemplary locking member that can be used to secure portions of a cord of support band material to one another and thereby form a loop.

FIG. 30 is a top view of another exemplary locking member that can be used to secure portions of a cord of support band material to one another and thereby form a loop.

FIG. 31 is a perspective view of an exemplary adjustment tool (or pusher tube) that can be used in connection with the locking member of FIG. 30.

DETAILED DESCRIPTION

General Considerations

Figure 1:
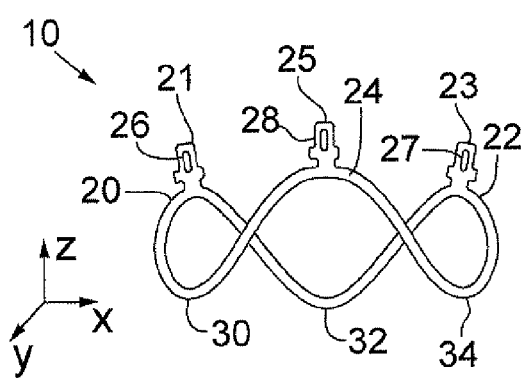
FIG. 1 is a perspective view of an exemplary embodiment of a support structure according to the disclosed technology.

Disclosed below are representative embodiments of a support structure (sometimes referred to as a "support stent," "support frame," "support band," or "support loop") that can be used to secure a prosthetic heart valve within a native heart valve. For illustrative purposes, embodiments of the support structure are described as being used to secure a transcatheter heart valve ("THV") in the aortic valve or the mitral valve of a heart. It should be understood that the disclosed support structure and THV can be configured for use with any other heart valve as well. Also disclosed herein are exemplary methods and systems for deploying the support structure and corresponding THV. Although the exemplary methods and systems are mainly described in connection with replacing an aortic or mitral valve, it should be understood that the disclosed methods and systems can be adapted to deliver a support structure and THV to any heart valve.

For illustrative purposes, certain embodiments of the support structure are described as being used in connection with embodiments of the balloon-expandable THV described in U.S. Patent Application Publication No. 2007/0112422 (U.S. application Ser. No. 11/280,063), which is hereby expressly incorporated herein by reference. It should be understood, however, that this particular usage is for illustrative purposes only and should not be construed as limiting. Instead, embodiments of the disclosed support structure can be used to secure a wide variety of THVs delivered through a variety of mechanisms (e.g., self-expanding heart valves, other balloon-expanding heart valves, and the like). For instance, any of the embodiments described in U.S. Pat. No. 6,730,118 can be used with embodiments of the disclosed support structure. U.S. Pat. No. 6,730,118 is hereby expressly incorporated herein by reference.

The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

Exemplary Embodiments for Replacing Aortic Valves

FIG. 1 is a perspective view showing an exemplary embodiment of a support stent or frame 10. Support stent 10 has a generally annular or torroidal body formed from a suitable shape-memory metal or alloy, such as spring steel, Elgiloy®, or Nitinol. Desirably, the material from which the support stent 10 is fabricated allows the support stent to automatically expand to its functional size and shape when deployed but also allows the support stent to be radially compressed to a smaller profile for delivery through the patient's vasculature. In other embodiments, however, the stent is not self expanding. In these embodiments, and as more fully explained below, other mechanisms for expanding the stent can be used (e.g., a balloon catheter).

In the illustrated embodiment, the projection of the support stent 10 onto an x-y plane has a generally annular or torroidal shape. The illustrated support stent 10 further defines a number of peaks and valleys (or crests and troughs) along its circumference. For example, the support stent 10 is sinusoidally shaped in the z direction. In other embodiments, the support stent 10 is shaped differently in the z direction (e.g., sawtooth-shaped, ringlet-shaped, square-wave shaped, or otherwise shaped to include peaks and valleys).

The illustrated support stent 10 includes three peaks 20, 22, 24 and three valleys 30, 32, 34. In the illustrated embodiment, the peaks 20, 22, 24 are positioned above the valleys 30, 32, 34 in the z direction. In some embodiments, the peaks have greater radii than the valleys 30, 32, 34, or vice versa. For instance, in some embodiments, the projection of the support stent 10 onto an x-y plane forms a closed shape having a variable radius (e.g., a starfish shape).

The size of the support stent 10 can vary from implementation to implementation. In particular embodiments, the support stent 10 is sized such that the support stent can be positioned within the aorta of a patient at a location adjacent to the aortic valve, thereby circumscribing the aortic valve. Furthermore, in order to frictionally secure a prosthetic heart valve in its interior, certain embodiments of the support stent 10 have a diameter that is equal to or smaller than the diameter of the prosthetic heart valve when fully expanded. In particular embodiments, for instance, the support stent can have an inner or outer diameter between 10 and 50 mm (e.g., between 17 and 28 mm) and a height between 5 and 35 mm (e.g., between 8 and 18 mm). Furthermore, the thickness of the annular body of the support stent 10 may vary from embodiment to embodiment, but in certain embodiments is between 0.3 and 1.2 mm.

Figure 2:
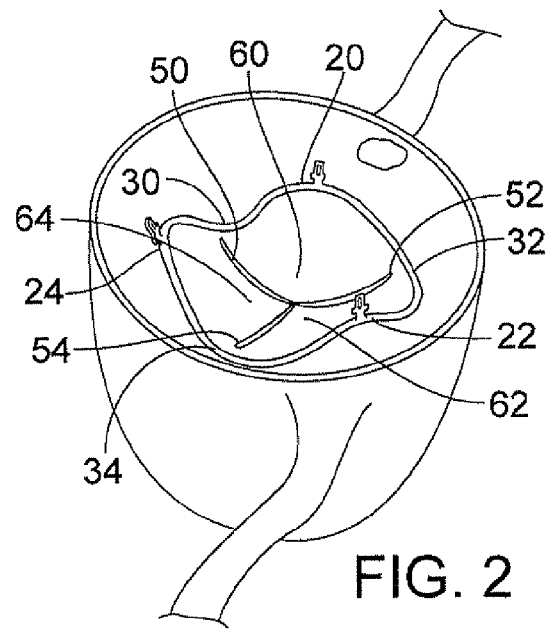
FIG. 2 is a cross-sectional view of a native aortic valve with the support structure of FIG. 1 positioned therein.

FIG. 2 is a perspective view of the exemplary support stent 10 positioned on the surface of an outflow side of a native aortic valve and further illustrates the shape of the support stent. In particular, it can be seen from FIG. 2 that the valleys 30, 32, 34 of the support stent 10 are shaped so that they can be placed adjacent to commissures 50, 52, 54 of the native leaflets 60, 62, 64 of the aortic valve. Furthermore, in the illustrated embodiment, the peaks 20, 22, 24 are shaped so that they generally approximate or mirror the size and shape of the leaflets 60, 62, 64 but are slightly smaller and lower than the height of the leaflets 60, 62, 64 at their tips when the aortic valve is fully opened. In other embodiments, the peaks 20, 22, 24 are oriented so that they are adjacent to the commissures 50, 52, 54 of the native leaflets 60, 62, 64 and the valleys are opposite the apexes of the leaflets 60, 62, 64. The support stent 10 can be positioned in any other orientation within the aortic valve as well. In the illustrated embodiment, no portion of the uncompressed support stent 10 extends into the aortic valve.

It should be understood that the shape of the support stent or frame 10 can vary from implementation to implementation. For example, in some embodiments, the support stent is not sinusoidal or otherwise shaped in the z-plane. In other embodiments, the support stent is shaped as a cylindrical band or sleeve. In general, the support stent or frame can be any shape that defines an interior through which a THV can be inserted, thereby causing the native leaflets of the aortic valve (or other heart valve) to be pinched or securely held between the support stent and the THV. Furthermore, the support stent can have a more complex structure. For example, although the support stent illustrated in FIGS. 1 and 2 is formed from a single annular member (or strut), the support stent can comprise multiple annular elements that interlock or are otherwise connected to one another (e.g., via multiple longitudinal members).

Returning to FIG. 1, the illustrated support stent 10 also include retaining arms 21, 23, 25 that can be used to help position and deploy the support stent 10 into its proper location relative to the native aortic valve. The retaining arms 21, 23, 25 can have respective apertures 26, 27, 28. An exemplary deployment system and procedure for deploying the support stent 10 using the retaining arms 21, 23, 25 are described in more detail below. The support stent 10 can also have one or more barbs located on its surface. Such barbs allow the support stent 10 to be more securely affixed to the tissue surrounding the stent or the leaflets of the aorta.

Figure 3:
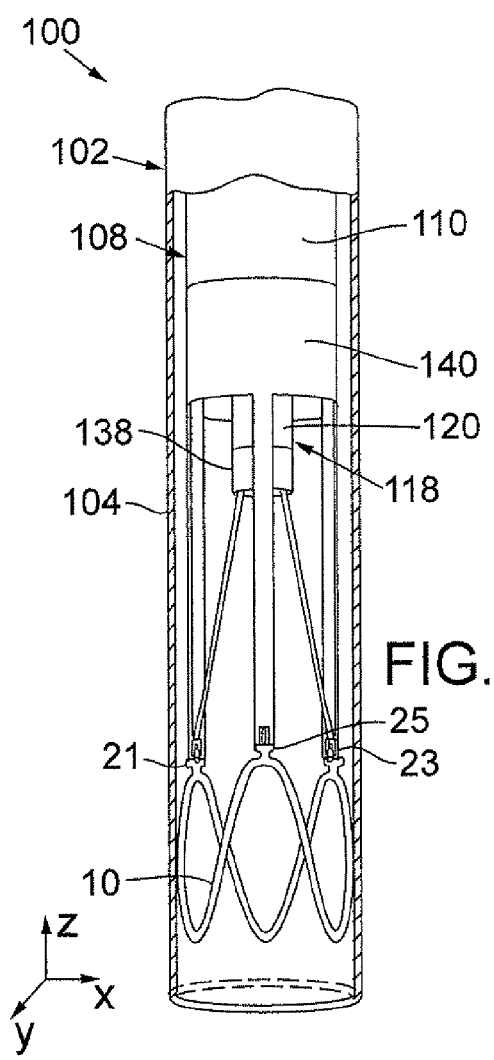
FIGS. 3 and 4 are perspective views of an exemplary delivery system for the support structure of FIG. 1. In particular.
Figure 4:
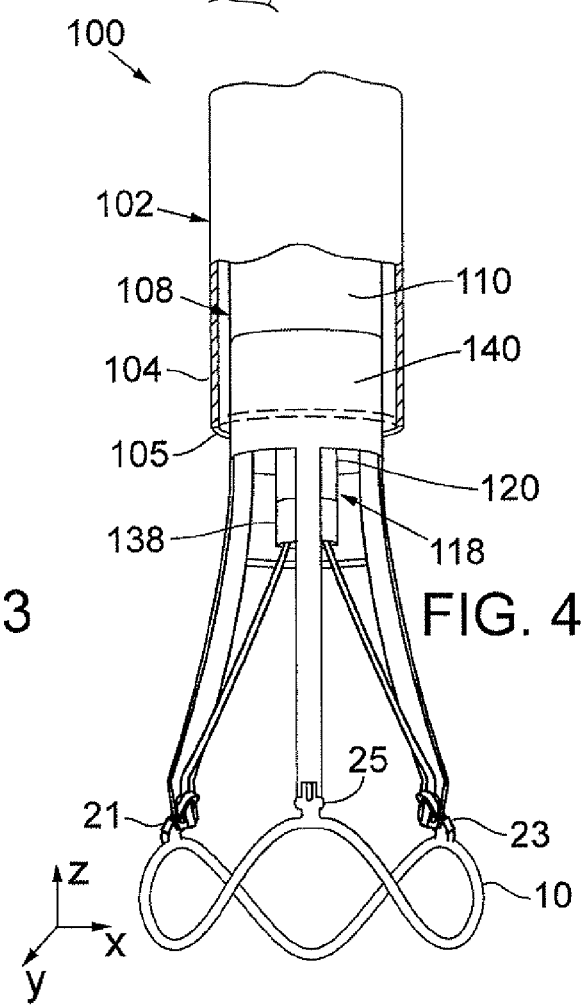

FIGS. 3 and 4 are side views of the distal end portion of an exemplary delivery apparatus 100 for delivering the support stent 10 to its location adjacent the native aortic valve through a patient's vasculature. In particular, FIG. 3 shows the delivery apparatus when the support stent 10 is in a compressed, predeployed state, whereas FIG. 4 shows the delivery apparatus when the support stent 10 is in a decompressed, deployed state. The delivery apparatus 100 comprises a guide catheter 102 having an elongated shaft 104, whose distal end 105 is open in the illustrated embodiment. In other embodiments, the distal end 105 of the guide catheter 102 can be tapered into a conical shape comprising multiple "flaps" forming a protective nose cone that can be urged apart when the support stent 10 and any interior catheters are advanced therethrough. Furthermore, for illustrative purposes, the guide catheter 102 is shown as being partially cut away, thus revealing the catheters in its interior.

A proximal end (not shown) of the guide catheter 102 is connected to a handle of the delivery apparatus 100. During delivery of a support stent, the handle can be used by a surgeon to advance and retract the delivery apparatus through the patient's vasculature. In a particular use, the delivery apparatus 100 is advanced through the aortic arch of a patient's heart in the retrograde direction after having been percutaneously inserted through the femoral artery. The guide catheter can be configured to be selectively steerable or bendable to facilitate advancement of the delivery system 100 through the patient's vasculature. An exemplary steerable guide catheter as can be used in embodiments of the disclosed technology is described in detail in U.S. Patent Application Publication No. 2007/0005131 (U.S. patent application Ser. No. 11/152,288), which is hereby expressly incorporated herein by reference.

The delivery apparatus 100 also includes a stent delivery catheter 108 positioned in the interior of the guide catheter 102. The stent delivery catheter 108 has an elongated shaft 110 and an outer fork 140 connected to a distal end portion of the shaft 110. The shaft 110 of the stent delivery catheter 108 can be configured to be moveable axially relative to the shaft 104 of the guide catheter 102. Furthermore, the shaft 110 of the stent delivery catheter 108 can be sized so that its exterior wall is adjacent to or in contact with the inner wall of the shaft 104 of the guide catheter 102.

The delivery apparatus 100 can also include an inner catheter 118 positioned in the interior of the stent deliver catheter 108. The inner catheter 118 can have an elongated shaft 120 and an inner fork 138 secured to the distal end portion of the shaft 120. The shaft 120 of the inner catheter 118 can be configured to be moveable axially relative to the shaft 104 of the guide catheter 102 and relative to the shaft 110 of the stent delivery catheter 108. Furthermore, the shaft 120 of the inner catheter 118 can be sized so that its exterior wall is adjacent to or in contact with the inner wall of the shaft 110 of the stent delivery catheter 108. A guide wire (not shown) can be inserted into the interior of the inner catheter 118. The guide wire can be used, for example, to help ensure proper advancement of the guide catheter 102 and its interior catheters through the vasculature of a patient.

Figure 5:
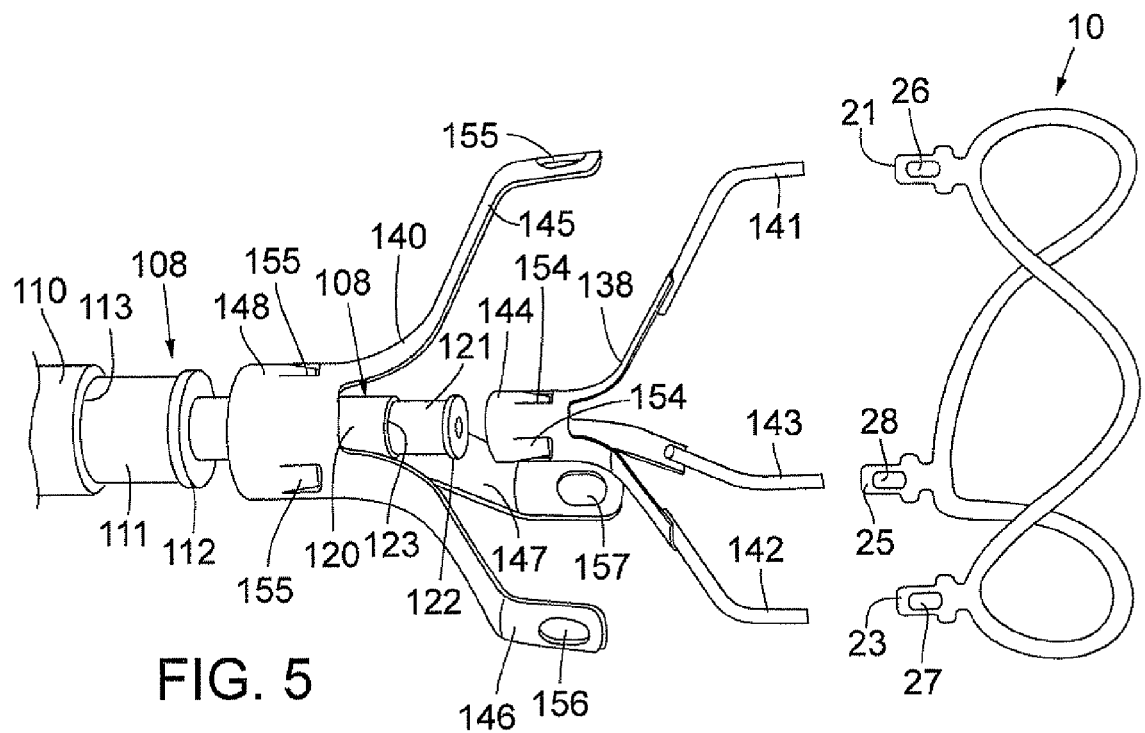
FIG. 5 is an exploded view of the components of the exemplary delivery system shown in FIGS. 3 and 4.

As best shown in FIG. 5, a stent retaining mechanism is formed from the inner fork 138 attached to the distal end portion of the shaft 120 of the inner catheter 118 and the outer fork 140 attached to the distal end portion of the shaft 110 of the stent delivery catheter 108. The inner fork 138 includes a plurality of flexible inner prongs 141, 142, 143 (three in the illustrated embodiment) at is distal end corresponding to the retaining arms 21, 23, 25 of the support stent 10, and a head portion 144 at its proximal end. The outer fork 140 includes a plurality of flexible outer prongs 145, 146, 147 (three in the illustrated embodiment) at its distal end corresponding to the retaining arms 21, 23, 25 of the stent 10, and a head portion 148 at its proximal end. The distal end portions of the outer prongs 145, 146, 147 are formed with respective apertures 155, 156, 157 sized to receive the retaining arms 21, 23, 25.

Figure 6:
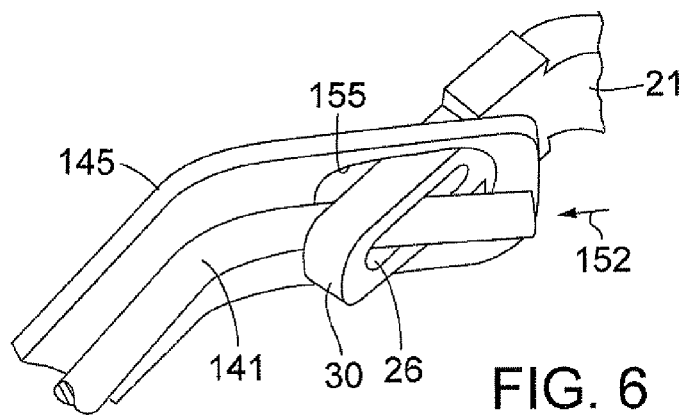
FIG. 6 is a zoomed-in perspective view showing the mechanism for releasably connecting the support structure to the exemplary delivery system of FIGS. 3 and 4.

FIG. 6 is a zoomed-in view of one of the retaining arms 21, 23, 25 as it interfaces with corresponding prongs of the outer fork 140 and the inner fork 138. In this example, retaining arm 21 is shown, though it should be understood that the retaining mechanism is similarly formed for the retaining arms 23, 25. The distal end portion of the outer prong 145 is formed with the aperture 155. When assembled, the retaining arm 21 of the stent is inserted through the aperture 155 of the prong 145 of the outer fork and the prong 141 of the inner fork is inserted through the aperture 26 of the retaining arm 21 so as to retain the retaining arm 21 in the aperture 155.

Retracting the inner prong 141 proximally (in the direction of arrow 152) to remove the prong from the aperture 26 allows the retaining arm 21 to be removed from the aperture 155, effectively releasing the retaining arm from the retaining mechanism. For instance, the outer prong 145 and the retaining arm 21 can be formed such that when the inner prong 141 is withdrawn from the aperture 26, the outer prong 145 flexes radially inward (downward in FIG. 7) and/or the retaining arm 21 of the support stent flexes radially outward (upward in FIG. 7), thereby causing the retaining arm 21 to be removed from the aperture 155. In this manner, the retaining mechanism formed by the inner fork 138 and the outer fork 140 create a releasable connection with the support stent 10 that is secure enough to retain the support stent to the stent delivery catheter 108 and to allow the user to adjust the position of the support stent after it is deployed. When the support stent 10 is positioned at the desired location adjacent to the leaflets of the aortic valve, the connection between the support stent and the retaining mechanism can be released by retracting the inner fork 138 relative to the outer fork 140, as further described below. In other embodiments, the function of the inner fork and the outer fork can be reversed. For example, the prongs of the inner fork can be formed with apertures sized to receive the corresponding retaining arms of the support stent and the prongs of the outer fork can be inserted through the apertures of the retaining arms when the retaining arms are placed through the apertures of the prongs of the inner fork.

As best shown in the exploded view in FIG. 5, the head portion 144 of the inner fork can be connected to the distal end portion of the shaft 120 of the inner catheter 118. In the illustrated embodiment, for example, the head portion 144 of the inner fork is formed with a plurality of angularly spaced, inwardly biased retaining flanges 154. An end piece of the shaft 120 can be formed as a cylindrical shaft having an annular groove 121. On the distal side of the annular groove 121, the shaft 120 can have a collar 122 with an outer diameter that is slightly greater than the diameter defined by the inner free ends of the flanges 154. Thus, the inner fork 138 can be secured to the end piece by inserting head portion 144 of the inner fork onto the end piece of the shaft 120 until the flanges 154 flex inwardly into the annular groove 121 adjacent the collar 122, thereby forming a snap-fit connection between the head portion 144 and the shaft 120. The head portion 144 can have a proximal end that engages an annular shoulder 123 of the shaft 120 that is slightly larger in diameter so as to prevent the head portion from sliding longitudinally along the shaft 120 in the proximal direction.

The head portion 148 of the outer fork can be secured to a distal end portion of the shaft 110 of the stent delivery catheter 108 in a similar manner. As shown in FIG. 5, the head portion 148 can be formed with a plurality of angularly spaced, inwardly biased retaining flanges 155. An end piece of the shaft 110 can be formed as a cylindrical shaft having an annular groove 111. On the distal side of the annular groove 111, the shaft 110 can have a collar 112 with an outer diameter that is slightly greater than the diameter defined by the free ends of the flanges 155. Thus, the outer fork 140 can be secured to the end piece of the shaft 110 by inserting the shaft 110 onto the head portion 148 until the flanges flex inwardly into the groove 111, thereby forming a snap-fit connection between the head portion 148 and the shaft 110. The head portion 148 can have a proximal end that engages an annular shoulder 123 of the shaft 110 that is slightly larger so as to prevent the head portion from sliding longitudinally along the shaft 110 in the proximal direction.

In FIG. 3, the support stent 10 is shown in a radially compressed state in the interior of the elongated shaft 104 of the guide catheter 102. In the radially compressed state, the distance along the z axis between a peak and an adjacent valley of the support stent is greater than the distance along the z axis between the peak and the adjacent valley when the support stent is in it uncompressed state. The distal end portion of the shaft 104 can also be referred to as a delivery sheath for the stent 10. In this undeployed and compressed state, the prongs of the outer fork 140 and the inner fork 138 of the stent delivery catheter 108 and the inner catheter 118 engage the retaining arms 21, 23, 25 of the support stent 10 in the manner described above with respect to FIGS. 5 and 6. To deploy the support stent 10 in the illustrated embodiment (advance the stent from the delivery system), the stent delivery catheter 108 and the inner catheter 118 are advanced toward the distal end 105 of the guide catheter 102 using one or more control handles or mechanisms (not shown) located at the proximal end of the guide catheter 102. This action causes the support stent 10 to be advanced outwardly through the distal end 105 of the guide catheter 102 and expand into its relaxed, uncompressed state (shown, for example, in FIGS. 1 and 2).

FIG. 4 is a perspective view showing the support stent 10 after it has been advanced from the distal end of the guide catheter 102. As seen in FIG. 4, the support stent 10 now assumes its relaxed, uncompressed shape but remains connected to the outer fork 140 and the inner fork 138 at its retaining arms 21, 23, 25. In this configuration, the support stent 10 can be rotated (in the clockwise or counter-clockwise directions) or repositioned (in the proximal and distal directions and/or into a different position in the x-y plane) into a proper orientation adjacent to its intended target area. For example, the support stent 10 can be positioned against the upper surfaces of leaflets of the aortic valve in the manner illustrated in FIG. 2 while the support stent 10 remains connected to the delivery system 100 via the retaining arms 21, 23, 25. As more fully illustrated below in FIGS. 7-12, a prosthetic valve (e.g., a THV) can be delivered to the aortic valve through a transapical approach (e.g., through the apex of the heart and through the left ventricle) and deployed within the native valve such that the prosthetic valve is secured in place by frictional engagement between the support stent, the native leaflets, and the prosthetic valve.

In particular embodiments, the support stent 10 is shaped so that the THV can be positioned in the interior of the support stent along with the native leaflets of the aortic valve. More specifically, the support stent 10 can be shaped such that the native leaflets become trapped or pinched between the support stent 10 and the exterior of the THV when the THV is installed. For instance, the diameter of the support stent 10 can be equal to or smaller than the maximum diameter of the THV when fully expanded, thus causing the THV to be frictionally fit to the leaflets of the aortic valve and the support stent 10. This friction fit creates a solid foundation for the THV that is independent of the state or condition of the leaflets in the aortic valve. For example, THVs are most commonly used for treating aortic stenosis, a condition in which the leaflets of the aortic valve become hardened with calcium. The hardened leaflets typically provide a good support structure for anchoring the THV within the aortic annulus. Other conditions may exist, however, in which it is desirable to implant a THV into the aortic valve and which do not result in a hardening of the leaflets of the aortic valve. For instance, the support stent 10 can be used as a foundation for a THV when treating patients with aortic insufficiency. Aortic insufficiency results when the aortic annulus dilates such that the aortic valve does not close tightly. With this condition, the aortic annulus is larger than normal and would otherwise require a large THV. Using a support stent or frame (such as the support stent or frame 10), however, a smaller THV can be used, thereby making the THV delivery process easier and safer. Furthermore, the use of a support stent protects against displacement of the THV if there is any further dilation of the aortic valve.

A support stent can be used to secure a THV in any situation in which the aorta or aortic valve may not be in condition to help support the THV and is not limited to cases of aortic insufficiency. For example, a support stent 10 can be used in cases in which the aortic annulus is too dilated or in which the leaflets of the aorta are too weak or soft. The support stent can be used to create an anchor for the THV, for instance, in cases in which the native leaflet tissue is too soft because of excess collagen in the aorta.

Figure 7:
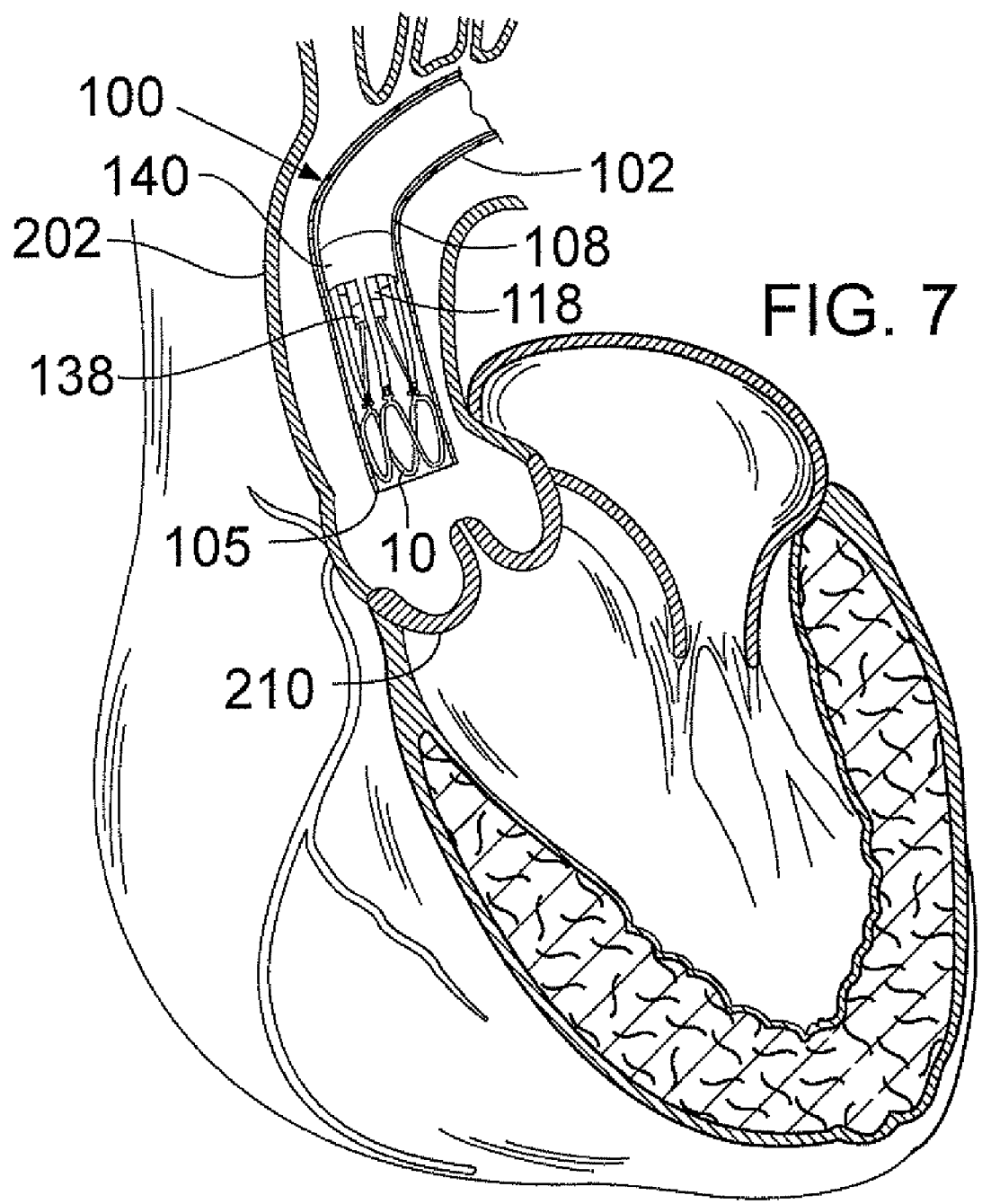
FIGS. 7 and 8 are cross-sectional views of a patient's heart illustrating how the delivery system of FIGS. 3 and 4 can operate to deploy the support structure of FIG. 1 to a desired position on the patient's aortic valve.
Figure 8:
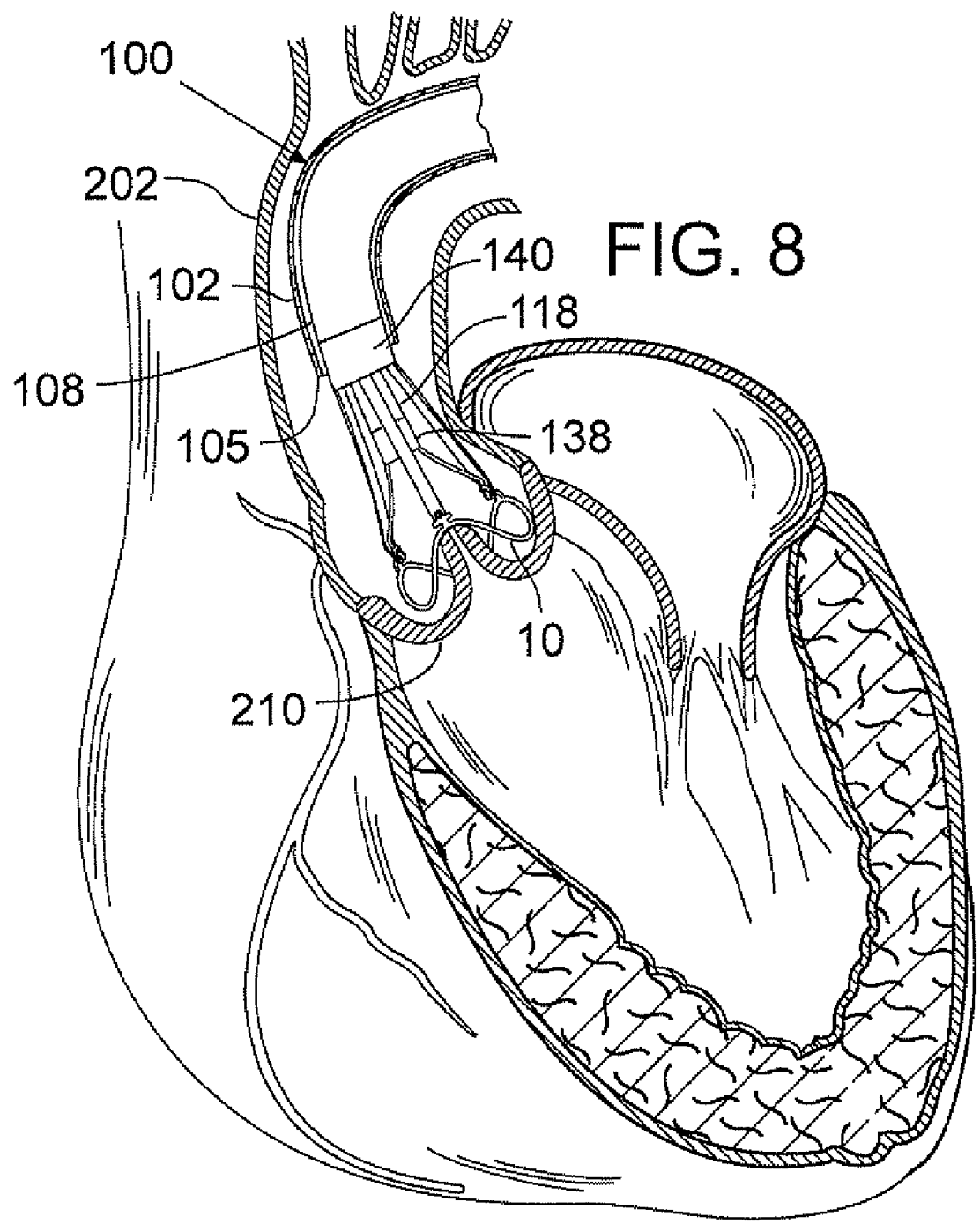

FIGS. 7-13 illustrate one exemplary procedure for deploying the support stent and securing a THV to the support stent. In particular, FIGS. 7-8 are cross-sectional views through the left side of a patient's heart showing the acts performed in delivering the support stent 10 through the aortic arch to the aortic valve. FIGS. 9-13 are cross-sectional views through the left side of a patient's heart showing the acts performed in deploying a THV 250 and having it engage the support stent 10. In order to better illustrate the components of the delivery system 100, the guide catheter 102 is shown partially cut away in FIGS. 7-13. For the sake of brevity, certain details concerning the delivery system of the THV 250 are omitted. Additional details and alternative embodiments of the delivery system for the THV 250 that may be used with the support stent described herein are discussed in U.S. Patent Application Publication No. 2007/0112422 (U.S. application Ser. No. 11/280,063), which is hereby expressly incorporated herein by reference.

FIG. 7 shows the guide catheter 102 of the delivery system 100 as it is advanced through the aortic arch 202 into a position near the surface of the outflow side of the aortic valve 210. The delivery system 100 can be inserted through the femoral artery of the patient and advanced into the aorta in the retrograde direction. FIG. 7 also shows the stent delivery catheter 108, the inner catheter 118, and the support stent 10. In FIG. 7, the support stent 10 is in its radially compressed, predeployment state. Also seen in FIG. 7 are the outer fork 140 and the inner fork 138, which couple the radially compressed support stent 10 to the distal ends of the stent delivery catheter 108 and the inner catheter 118, respectively.

FIG. 8 shows the support stent 10 after it has been advanced through the distal end of the guide catheter 102 and assumes its final, uncompressed shape in a position above and adjacent to the aortic valve 210. The support stent 10 can also be placed directly on the surface of the outflow side of the aortic valve. FIG. 8 shows that the stent delivery catheter 108 and the inner catheter 118 have been advanced though the distal end of the guide catheter 102, thereby pushing the support stent 10 out of the guide catheter and allowing it to expand into its natural shape. In particular embodiments, the support stent 10 is rotated and positioned as necessary so that the support stent generally circumscribes the aortic valve and so that the peaks of the support stent are aligned with the tips of the natural leaflets of the aortic valve 210. Therefore, when the THV is inserted and expanded within the aortic valve 210, the leaflets of the aortic valve will engage at least the majority of the surface in the interior of the support stent 10. This alignment will create an overall tighter fit between the support stent 10 and the THV. In other embodiments, the support stent 10 is rotated and positioned as necessary so that the peaks of the support stent 10 are aligned with the commissures or other portions of the aortic valve. The position of the guide catheter 102 and the support stent 10 relative to the aortic valve 210, as well as the position of other elements of the system, can be monitored using radiopaque markers and fluoroscopy, or using other imaging systems such as transesophageal echo, transthoracic echo, intravascular ultrasound imaging ("IVUS"), or an injectable dye that is radiopaque.

Also seen in FIG. 8 are the prongs of the outer fork 140 and the prongs of the inner fork 138. In the exemplary procedure, the prongs of the outer fork 140 and the inner fork 138 remain secured to the support stent 10 until the THV is deployed and frictionally engaged to the support stent. The inner and outer forks desirably form a connection between the stent 10 and the delivery system that is secure and rigid enough to allow the surgeon to hold the stent 10 at the desired implanted position against the flow of blood while the THV is being implanted.

In FIG. 8, the support stent 10 is self-expanding. In other embodiments, however, the support stent may not be self-expanding. In such embodiments, the support stent can be made of a suitable ductile material, such as stainless steel. In addition, a mechanism for expanding the support stent can be included as part of the delivery system 100. For example, the support stent can be disposed around a balloon of a balloon catheter in a compressed state. The balloon catheter can have a shaft that is interior to the inner catheter 118. Because the stent 10 is not self-expanding, the distal end portion of the guide catheter 102 need not extend over the compressed support stent. During delivery of the support stent, the support stent, balloon catheter, inner catheter 118, and stent delivery catheter 108 can be advanced from the distal end of the guide catheter 102. The balloon portion of the balloon catheter can be inflated, causing the support stent to expand. The balloon portion can subsequently be deflated and the balloon catheter withdrawn into the delivery system 100 to remove the balloon from the interior of the support stent while the support stent remains connected to the inner catheter for positioning of the support stent. The delivery of the support stent otherwise proceeds as in the illustrated embodiment using the self-expanding support stent 10.

Figure 9:
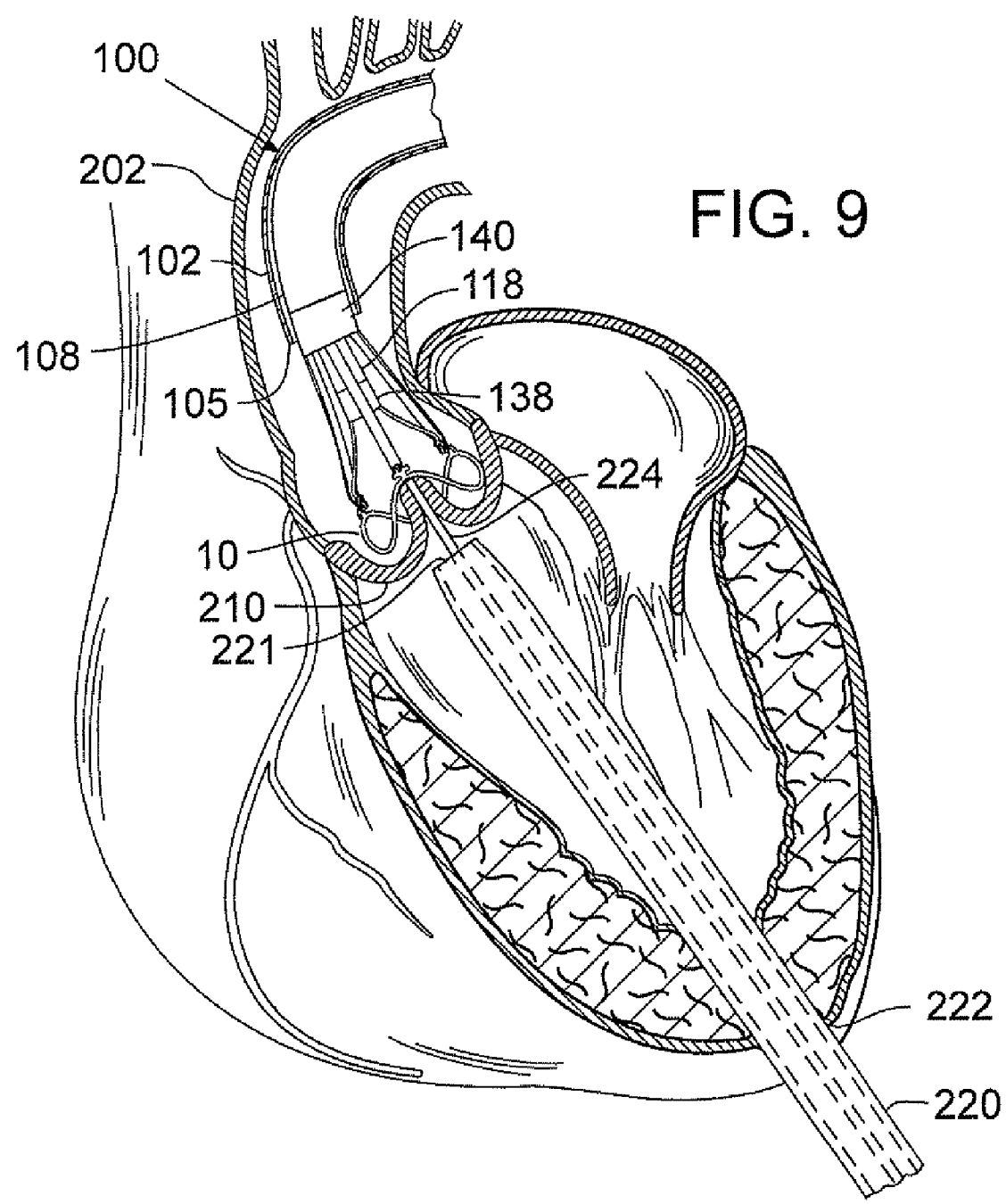
FIGS. 9-13 are cross-sectional views of a patient's heart illustrating how an exemplary transcatheter heart valve ("THV") can be deployed to the patient's aortic valve and frictionally secured to the native leaflets using the support structure of FIG. 1.

FIG. 9 shows an introducer sheath 220 passing into the left ventricle through a puncture 222 and over a guidewire 224 that extends upward through the aortic valve 210. The surgeon locates a distal tip 221 of the introducer sheath 220 just to the inflow side of the aortic valve 210. The position of the introducer sheath 220 relative to the aortic valve 210, as well as the position of other elements of the system, can be monitored using radiopaque markers and fluoroscopy, or using other imaging systems.

Figure 10:
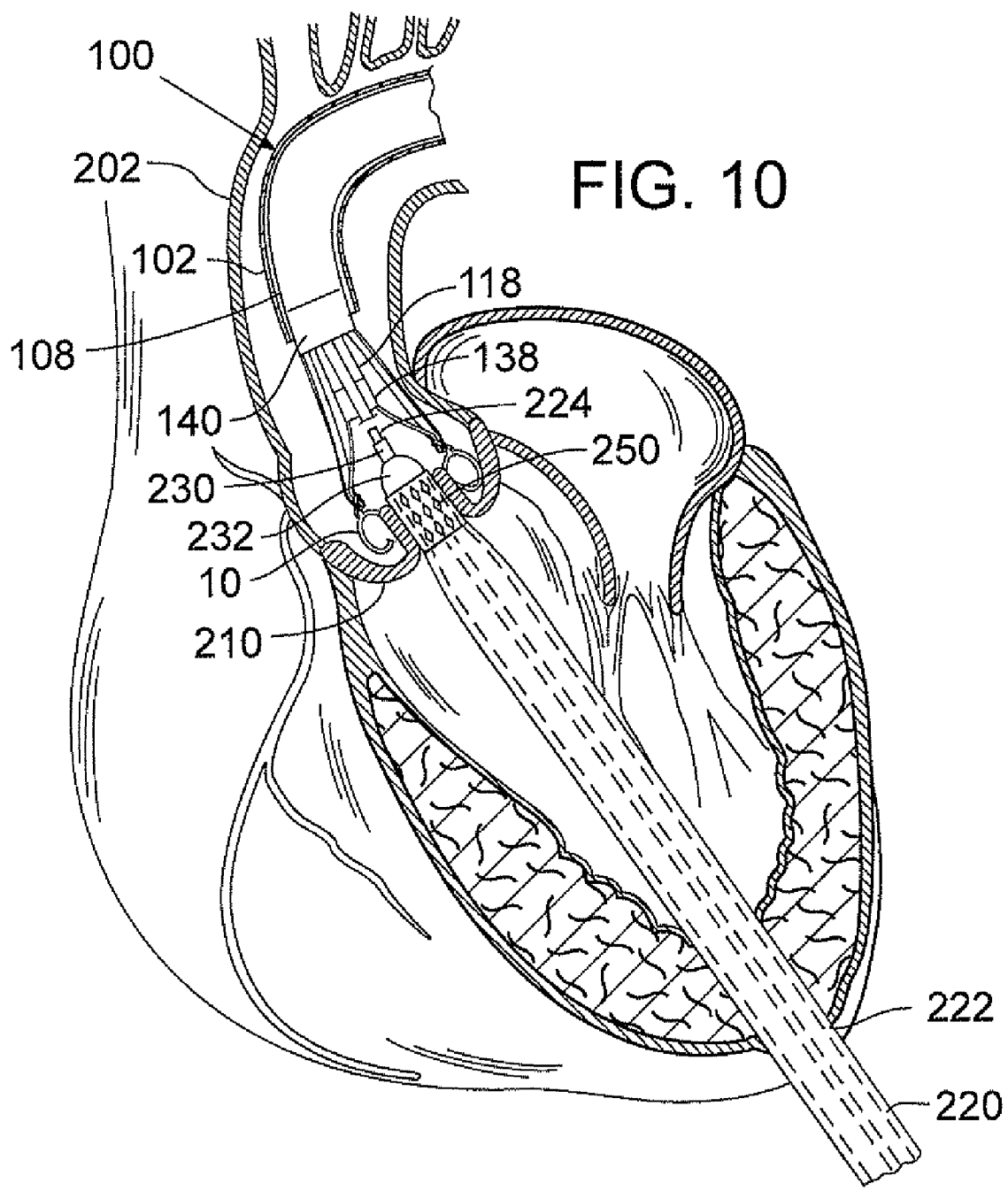
Figure 11:
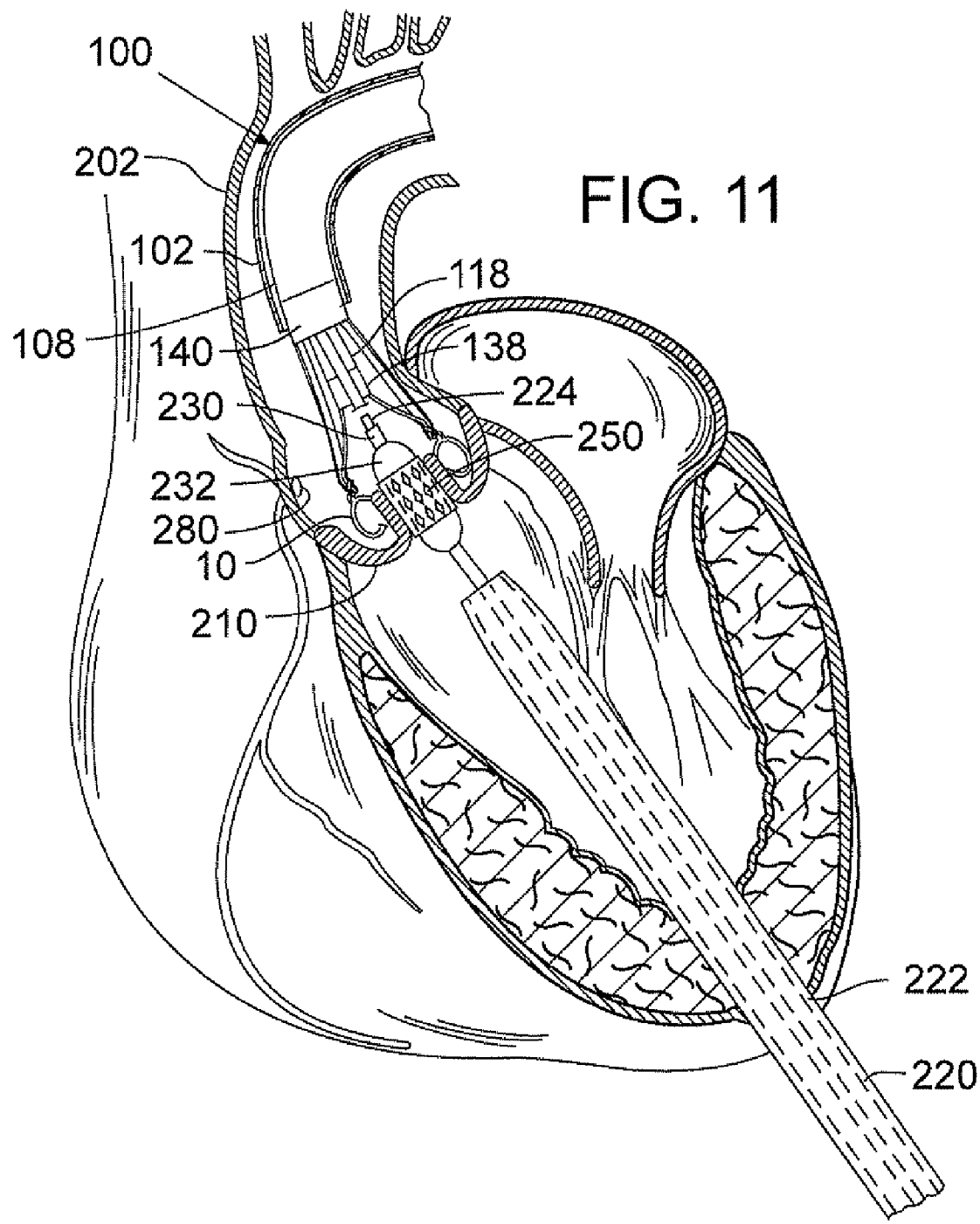
Figure 12:
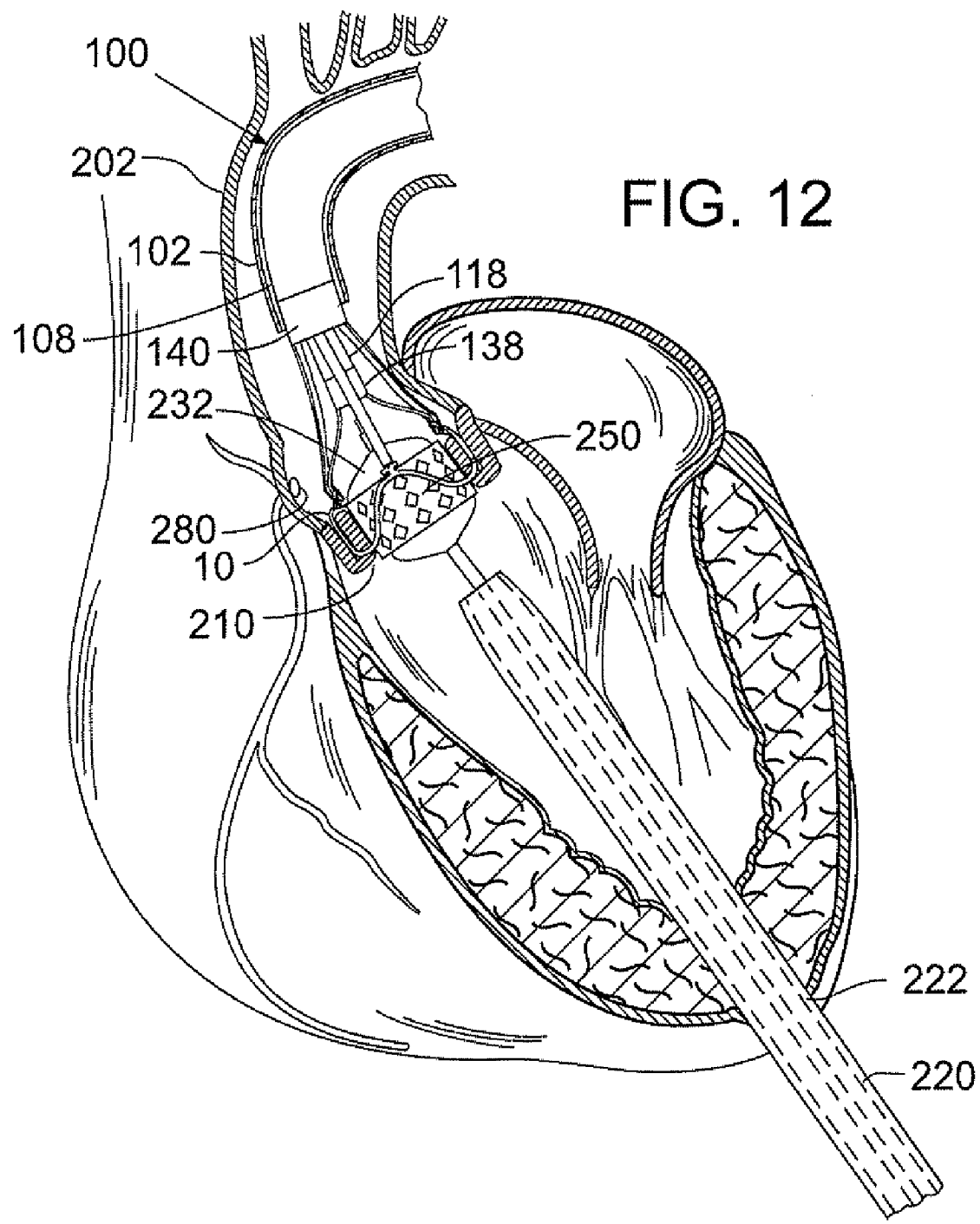
Figure 13:
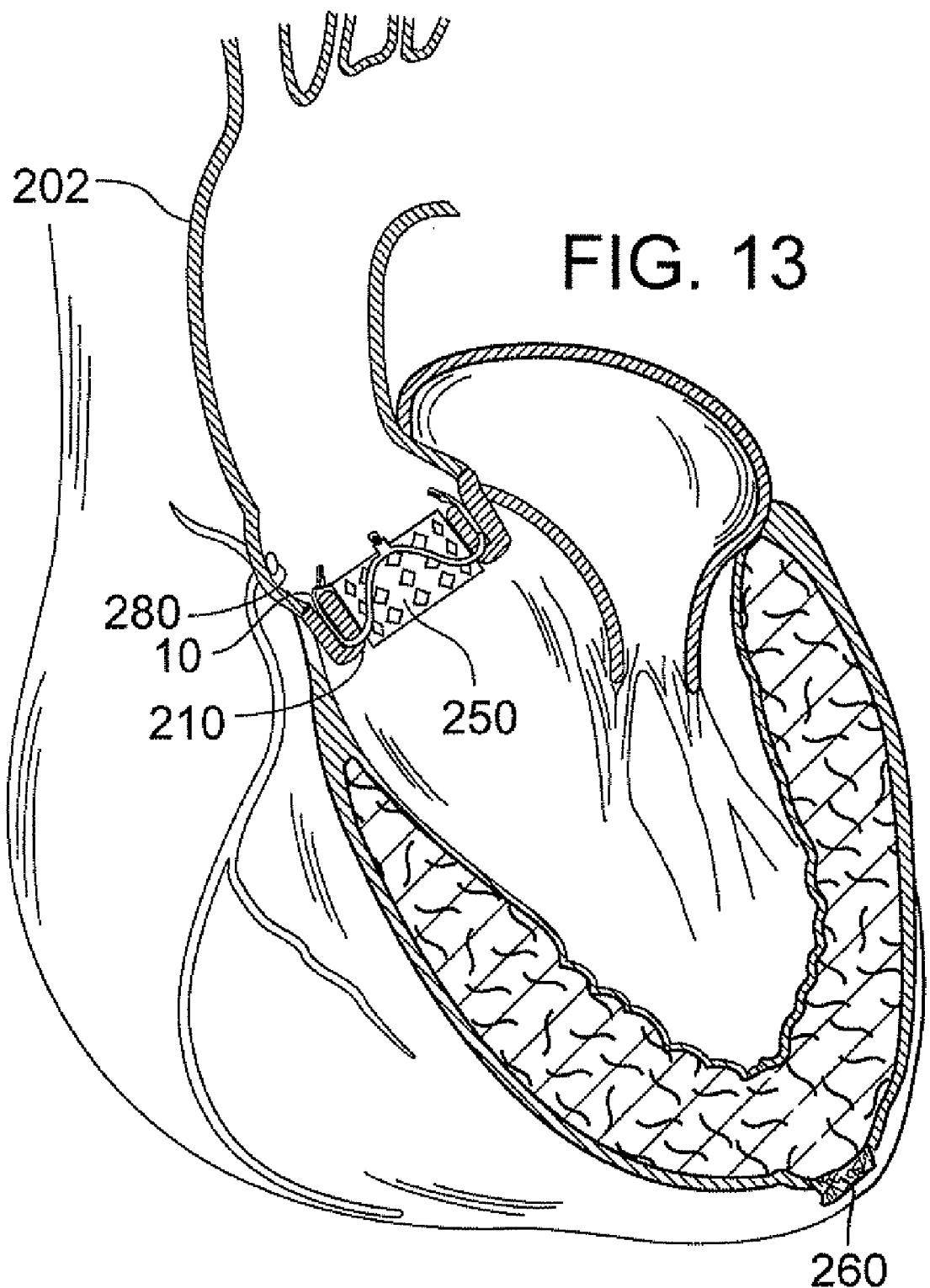

FIG. 10 shows the advancement of the balloon catheter 230 over the guidewire 224 and through the introducer sheath 220. Ultimately, as seen in FIG. 11, the THV 250 is located at the aortic annulus and between the native aortic leaflets. FIG. 11 also illustrates retraction of the introducer sheath 220 from its more distal position in FIG. 10. Radiopaque markers may be provided on the distal end of the introducer sheath 220 to more accurately determine its position relative to the valve 210 and balloon 232. In order to better illustrate the components of the delivery system for the THV, FIGS. 10-11 do not show the front third of the support stent 10 or the corresponding outer and inner prong of the outer fork and the inner fork, respectively. Furthermore, for purpose of illustrating the relative position of the support stent 10 on the THV 250, FIGS. 12-13 show the front third of the support stent 10 and the front of the THV 250, but do not show the portions of the native heart valve that would be secured by the front of the support stent 10. It is to be understood, however, that a corresponding leaflet of the native heart valve would be secured between the support stent 10 and the THV 250.

Again, the precise positioning of the THV 250 may be accomplished by locating radiopaque markers on its distal and proximal ends. In some embodiments, the surgeon can adjust the position of the valve 250 by actuating a steering or deflecting mechanism within the balloon catheter 230. Furthermore, the rotational orientation of the valve 250 can be adjusted relative to the cusps and commissures of the native aortic valve by twisting the balloon catheter 230 from its proximal end and observing specific markers on the valve (or balloon catheter) under fluoroscopy. One of the coronary ostia 280 opening into one of the sinuses of the ascending aorta is also shown in FIG. 11, and those of skill in the art will understand that it is important not to occlude the two coronary ostia with the prosthetic valve 250.

FIG. 11 shows the THV 250 in its contracted or unexpanded state crimped around the balloon 232. When the surgeon is satisfied of the proper positioning and rotational orientation of the valve 250, the balloon 232 is expanded to engage the support stent 10 as seen in FIG. 12. The engagement of the support stent 10 to the exterior of the THV 250 pinches the leaflets of the aortic valve between the support stent and the THV 250, and thereby secures the THV within the annulus of the aortic valve. Once secured into this position, the inner catheter 118 of the delivery system 100 can be retracted, thereby causing the prongs of the inner fork 138 to become disengaged from the retaining arms of the support stent 10. Once the prongs of the inner fork 138 are disengaged, the prongs of the outer fork 140 can be disengaged from the retaining arms by retracting the stent delivery catheter 108. Once disengaged from the support stent, the delivery system 100 can be retracted from the aortic arch and removed from the patient.

It should be noted that the valve 250 can take a variety of different forms and may comprise an expandable stent portion that supports a valve structure. The stent portion desirably has sufficient radial strength to hold the valve at the treatment site and to securely engage the support stent 10. Additional details regarding balloon expandable valve embodiments that can be used in connection with the disclosed technology are described in U.S. Pat. Nos. 6,730,118 and 6,893,460, both of which are hereby expressly incorporated herein by reference.

Once the valve 250 is properly implanted, as seen in FIG. 13, the balloon 232 is deflated, and the entire delivery system including the balloon catheter 230 is withdrawn over the guidewire 224. The guidewire 224 can then be withdrawn, followed by the introducer sheath 220. Ultimately, purse-string sutures 260 at the left ventricular apex can be cinched tight and tied to close the puncture.

FIGS. 14-16 shows another embodiment of a support stent or frame 310 that can be used to help secure a THV into the interior of a native heart valve, such as the aortic valve. In particular, FIG. 14 is a perspective view of the support stent 310, FIG. 15 is a top view of the support stent 310, and FIG. 16 is a side view of the support stent 310. Like support stent 10, support stent 310 has a generally annular or torroidal body formed from a suitable shape-memory metal or alloy, such as spring steel, Elgiloy®, or Nitinol. The support stent 310 is also radially compressible to a smaller profile and can self expand when deployed into its functional size and shape. In other embodiments, however, the support stent 310 is not self expanding.

The support stent 310 includes a generally cylindrical main body portion 320 and a rim portion 330. The support stent 310 can be a mesh structure, which can be formed, for example, from multiple elements in which approximately half of the elements are angled in a first direction and approximately half of the elements are angled in a second direction, thereby creating a criss-cross or diamond-shaped pattern. In the illustrated embodiment, the rim portion 330 has a greater diameter than the main body portion 320 and is formed as an extension at a bottom region of the main body portion that is folded outwardly from the main body portion and back toward a top region of the main body portion. The rim portion 330 thus forms a U-shaped rim or lip around the bottom region of the support stent 310. In general, the rim portion 330 is designed to have a diameter that is slightly larger than the walls of the aortic arch that surround the aortic valve. Thus, when the support stent 310 is delivered to the aortic valve and deployed at the aorta, the rim portion 330 expands to engage the surrounding aorta wall and frictionally secures the support stent 310. At the same time, the main body portion 320 defines an interior into which an expandable THV can be expanded and which further engages the native leaflets of the aortic valve. Thus, the main body portion 320 operates in the same manner as the support stent 10 described above and illustrated in FIGS. 1-12, whereas the rim portion 330 of the support stent 310 operates to secure the support stent in place by engaging the walls of the aorta that surround the aortic valve.

As best seen in FIGS. 14 and 16, the support stent 310 further includes retaining arms 321, 322, 323 that can be used to help position and deploy the support stent 310 into its proper location relative to the native aortic valve. The retaining arms 321, 322, 323 can have respective apertures 326, 327, 328. In general, the retaining arms 321, 322, 323 are constructed and function in a similar manner as retaining arms 21, 23, 25 described above in the embodiment illustrated in FIGS. 1-12.

Figure 17:
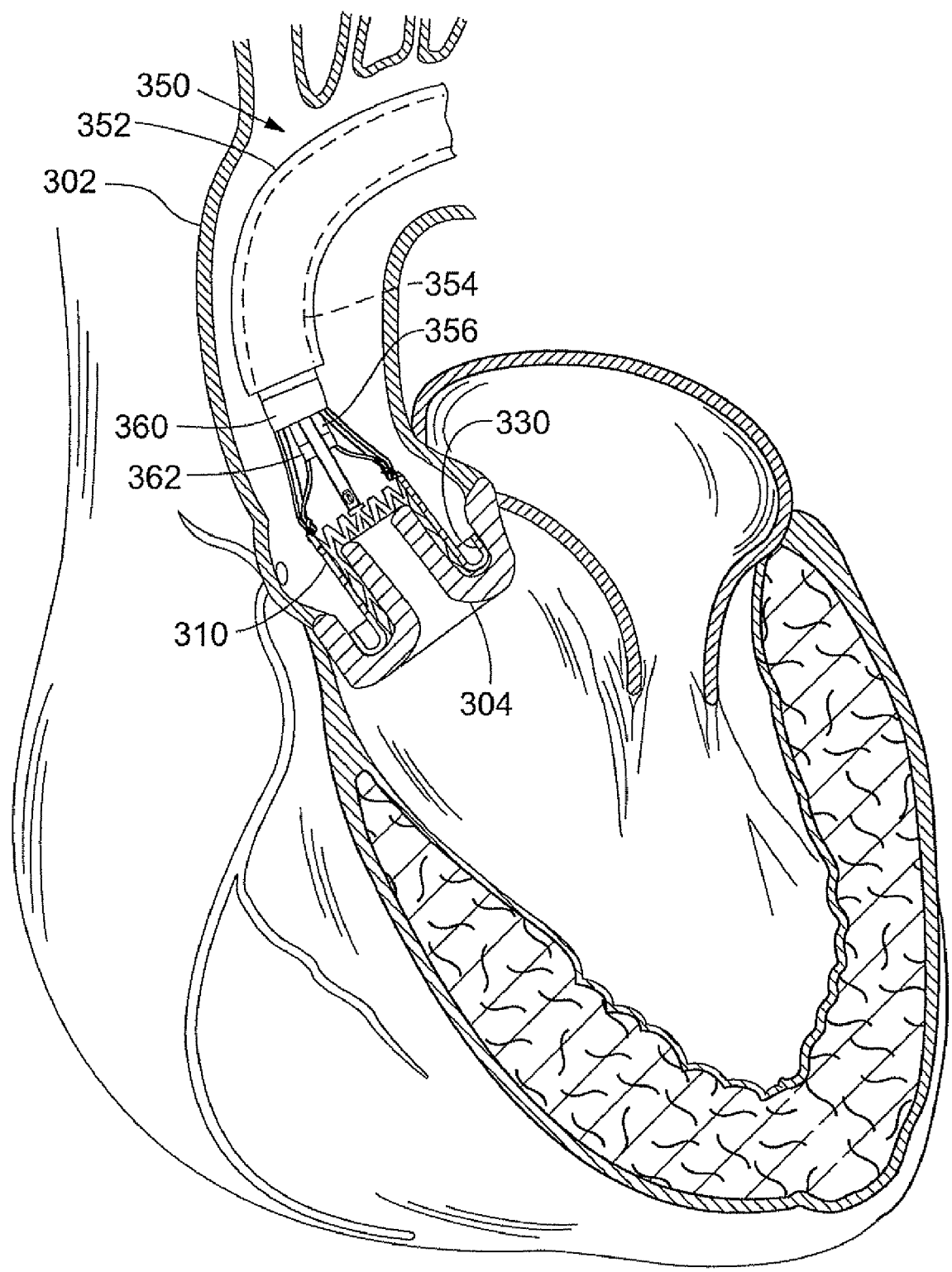
FIG. 17 is a cross-sectional view of a patient's heart illustrating how a delivery system can operate to deploy the support structure of FIG. 14 to a desired position on the patient's aortic valve.
Figure 18:
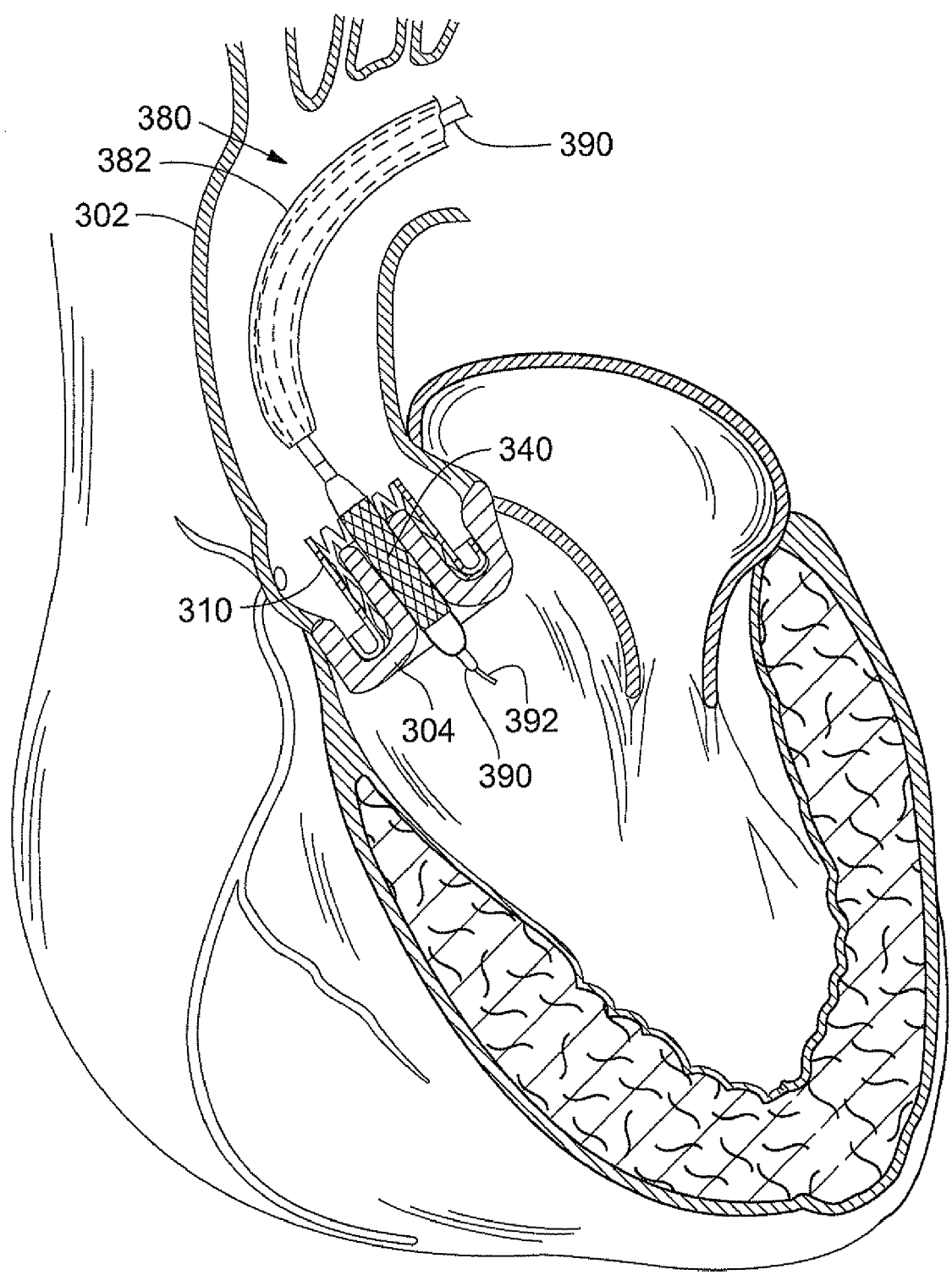
FIG. 18 is a cross-sectional view of a patient's heart illustrating how an exemplary THV can be deployed through the aortic arch and into the patient's aortic valve, where it can be frictionally secured to the native leaflets using the support structure of FIG. 14.

FIGS. 17-18 illustrate one exemplary procedure for deploying the support stent 310 and securing a THV 340 within an interior of the support stent. In particular, FIGS. 17-18 are cross-sectional views through the left side of a patient's heart showing the acts performed in delivering the support stent 310 through the aortic arch to the aortic valve. For the sake of brevity, certain details concerning the delivery system of the THV 340 are omitted. Additional details and alternative embodiments of the delivery system for the THV 340 that may be used with the support stent described herein are discussed in U.S. Patent Application Publication No. 2008/0065011 (U.S. application Ser. No. 11/852,977) and U.S. Patent Application Publication No. 2007/0005131 (U.S. application Ser. No. 11/152,288), which are hereby expressly incorporated herein by reference.

FIG. 17 shows an outer catheter 352 (which can be a guide catheter) of a delivery system 350 as it is advanced through the aortic arch 302 into a position near the surface of the outflow side of the aortic valve 304. The delivery system 350 can be inserted through the femoral artery of the patient and advanced into the aorta in the retrograde direction. FIG. 17 also shows a stent delivery catheter 354, an inner catheter 356, and the support stent 310. Also seen in FIG. 17 are the outer fork 360 and the inner fork 362, which couple the support stent 310 to the distal ends of the stent delivery catheter 354 and the inner catheter 356, respectively.

More specifically, FIG. 17 shows the support stent 310 after it has been advanced through the distal end of the guide catheter 352 and assumes its final, uncompressed shape in a position adjacent to the aortic valve 304. In order to better illustrate the components of the delivery system for the THV, FIGS. 17-18 do not show the entire front side of the support stent 310 or the corresponding valve leaflet that would be secured by the front side of the support stent 310. It is to be understood, however, that in practice the entire support stent 310 would exist and engage a corresponding leaflet of the native heart valve.

The support stent 310 can be positioned adjacent to the aortic valve 304 so that the rim portion 330 of the support stent engages the walls surrounding the aortic valve 304 and exerts an outward force against those walls, thereby securing the support stent 310 within the aorta. This positioning can be achieved, for example, by advancing the guide catheter 352 to a position directly adjacent the aortic valve 304 while the stent delivery catheter 354 and the inner catheter 356 are undeployed and while the support stent 310 remains in its compressed state. The guide catheter 352 can then be retracted while the stent delivery catheter 354 and the inner catheter 356 are held in place, thereby allowing the support stent 310 to expand toward its natural shape. As with the delivery system 100 described above, the position of the guide catheter 352 and the support stent 310 relative to the aortic valve 304, as well as the position of other elements of the system, can be monitored using radiopaque markers and fluoroscopy, or using other imaging systems such as transesophageal echo, transthoracic echo, IVUS, or an injectable dye that is radiopaque.

Once the support stent 310 is positioned into the desired location adjacent the aortic valve 304, the prongs of the inner fork 362 can be disengaged from the corresponding apertures of the retaining arms of the support stent 310. For example, the inner catheter 356 can be retracted into the interior of the stent delivery catheter 354, thereby releasing the support stent 310 from the outer fork 360 and the inner fork 362. The delivery system 350 can then be retracted from the aorta and removed from the patient's body.

With the support stent 310 secured to the aortic valve, a THV (such as any of the THVs discussed above) can be introduced. In contrast to the procedure illustrated in FIGS. 7-13, a delivery system having a delivery catheter that is advanced through the patient's aorta can be used to deliver the THV. In other words, a transfemoral approach can be used. For instance, any of the exemplary systems and methods described in U.S. Patent Application Publication No. 2008/0065011 (U.S. application Ser. No. 11/852,977) or U.S. Patent Application Publication No. 2007/0005131 (U.S. application Ser. No. 11/152,288) can be used with the support stent 310. Alternatively, the transapical approach shown in FIGS. 7-13 can be used.

FIG. 18 shows delivery system 380 comprising an outer catheter 382 (which can be a guide catheter) and a balloon catheter 390 extending through the guide catheter. The balloon catheter 390 has a balloon at its distal end on which the THV is mounted. As with the delivery system 350, the delivery system 380 can be inserted through the femoral artery of the patient and advanced into the aorta in the retrograde direction. FIG. 18 further shows a guidewire 392 that has been first inserted into the patient's vasculature and advanced into the left ventricle. The delivery system can then be inserted into the body and advanced over the guidewire 392 until the THV is positioned within the interior of the aortic valve. As shown, the THV is not only in the interior of the aortic valve 304 but also in the interior of the main body portion of the support stent 310.

FIG. 18 shows the THV 340 in its contracted (or unexpanded) state crimped around the balloon portion of the balloon catheter 390. When the surgeon is satisfied of the proper positioning, the balloon of the balloon catheter 390 can be expanded such that the THV 340 expands and urges the native leaflets of the aortic valve against the support stent 310, thereby securing the THV within the annulus of the aortic valve. Once the THV 340 is properly implanted, the balloon of the balloon catheter 390 is deflated, and the entire delivery system 380 including the balloon catheter is withdrawn over the guidewire 392. The guidewire 392 can then be withdrawn.

Other methods of delivering a support stent and THV to the aortic valve or any other heart valve are also possible. For example, in certain embodiments, the support stent and the THV are delivered surgically to the desired heart valve (e.g., in an open-heart surgical procedure). Furthermore, in certain embodiments in which the support stent and THV are delivered surgically, non-compressible support stents and/or THVs are used.

Exemplary Embodiments for Replacing Mitral Valves

The mitral valve can also suffer from valve insufficiency, which may be desirably treated through the implantation of a prosthetic valve. As with aortic valve insufficiency, mitral valve insufficiency often causes the valve annulus to be dilated and the valve leaflets to be too soft to provide reliable support for securing a prosthetic valve. Accordingly, and according to certain exemplary embodiments of the disclosed technology, it is desirable to use a support structure to help secure a transcatheter heart valve ("THV") within a patient's mitral valve. As with the support stents and frames described above, the mitral valve support structure is desirably positioned on the outflow side of the mitral valve. The THV can be inserted into the interiors of the native mitral valve and the support structure and then expanded such that the mitral valve leaflets are frictionally engaged between the exterior surface of the THV and the interior surface of the support structure. Alternatively, the support structure can be deployed after the THV is positioned and expanded within the mitral valve. The diameter of the support structure can then be adjusted such that the valve leaflets are frictionally engaged against the exterior of the THV. By using a support structure to secure the THV, a smaller THV can be used, thereby making the THV delivery process easier and safer. Furthermore, the use of a support structure protects against displacement of the THV if there is any further dilation of the aortic valve. Moreover, when a support structure is used to secure the THV, the native leaflets function as a sealing ring around the valve that prevents paravalvular leaks.

The support structure for the mitral valve can have a variety of shapes. For example, in some embodiments, the support structure has a sinusoidal shape as with the support stent 110, but in other embodiments does not have a sinusoidal shape or is not otherwise shaped in the z-plane. In further embodiments, the support stent is shaped as a cylindrical band or sleeve. The support frame can also have a more complex structure. In general, any of the shapes and materials used for embodiments of the aortic valve support structures described above can be used for embodiments of the mitral valve support structures and vice versa.

In one exemplary embodiment, the mitral valve support structure is made of a suitable biocompatible material that can be delivered through one or more delivery catheters and formed into a band or loop. For this reason, the structure is sometimes referred to herein as a "support band" or "support loop." The biocompatible material may comprise, for example, nylon, silk, polyester, or other synthetic biocompatible material. The biocompatible material may alternatively comprise a natural material, such as catgut. In still other embodiments, the support structure is formed of a biocompatible shape-memory metal or alloy, such as spring steel, Elgiloy®, or Nitinol.

Figure 23:
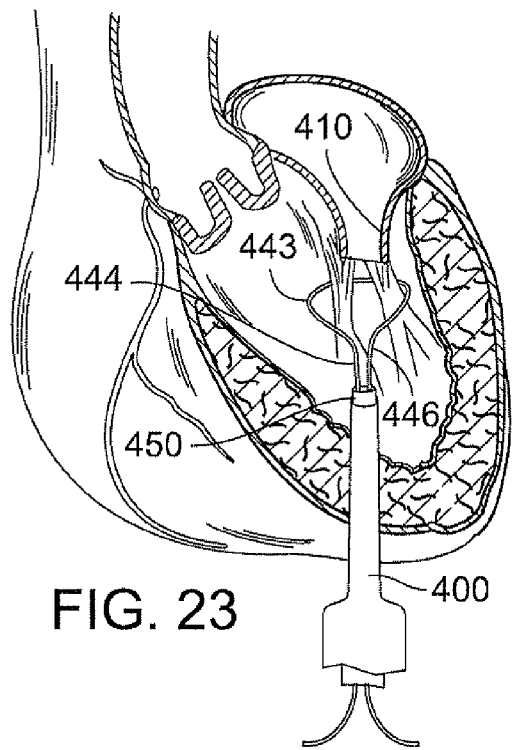
Figure 24:
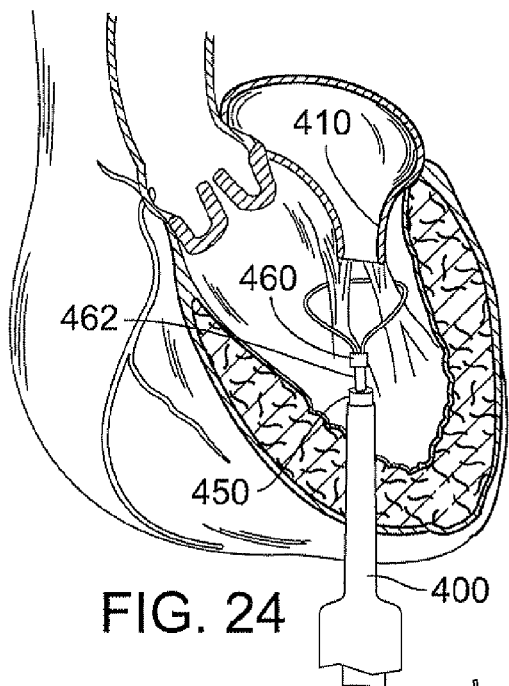
Figure 25:
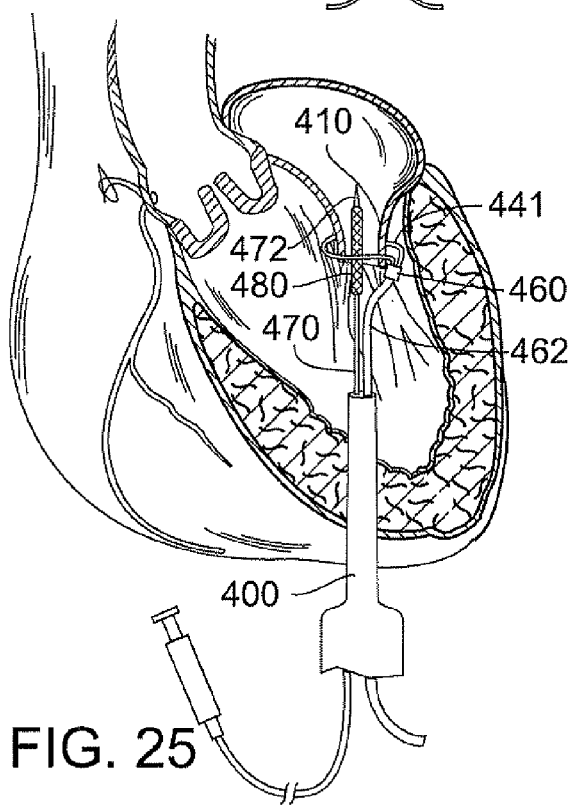
Figure 26:
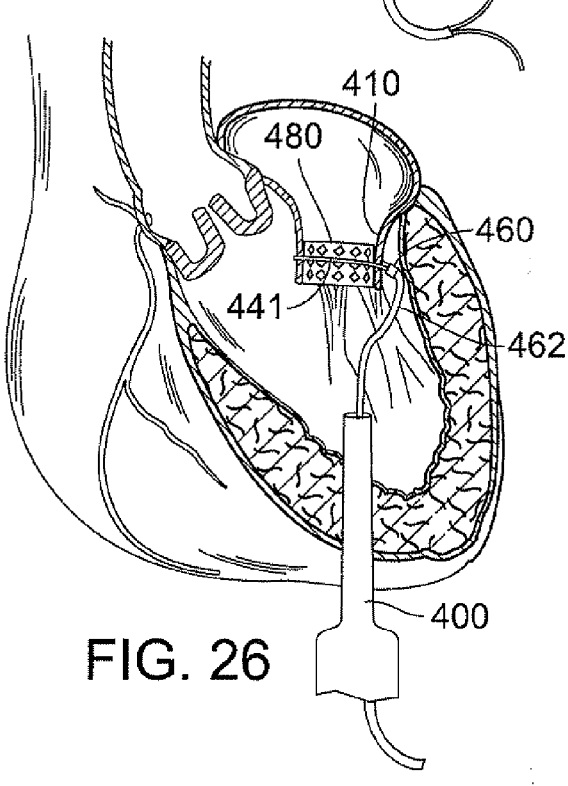
Figure 27:
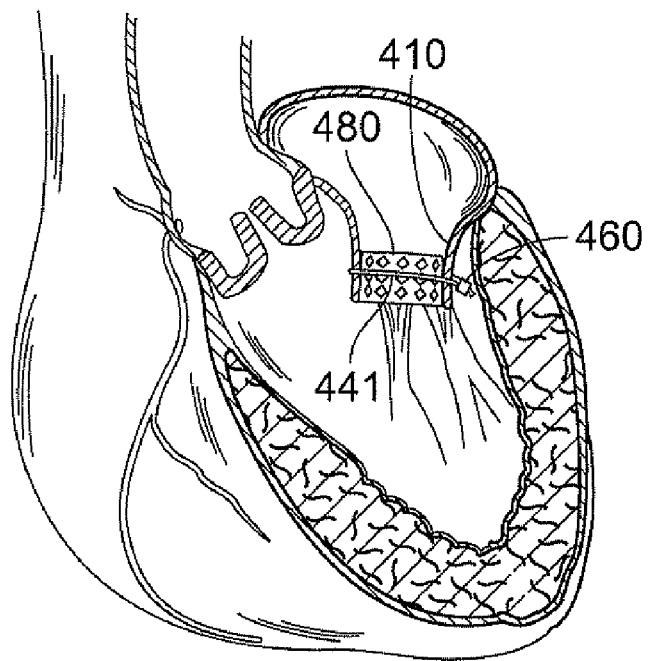

FIGS. 19-27 show one exemplary procedure for delivering a support structure to the mitral valve and having it secure a THV into its desired position within the mitral valve. In particular, FIGS. 19-24 are cross-sectional views through the left side of a patient's heart showing the acts performed in delivering the support structure using a transapical approach. FIGS. 25-27 are cross-sectional views through the left side of a patient's heart showing the acts performed in deploying a THV and having it engage the mitral valve leaflets and the interior of the support structure. It should be noted that FIGS. 19-27 are schematic in nature and thus do not necessarily depict a precise representation of the delivery process. For example, the patient's ribcage is not shown for illustrative purposes and the size of the sheaths used with the delivery system have been altered somewhat in order to better illustrate the procedure. One of ordinary skill in the art, however, will readily understand the range and types of sheaths and catheters that can be used to implement the depicted procedure.

Figure 19:
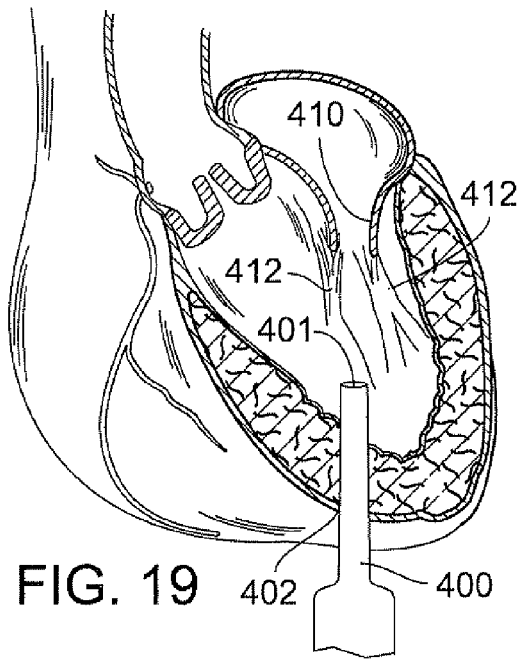
FIGS. 19-27 are cross-sectional view of a patient's heart illustrating how an exemplary support band can be deployed around the native leaflets of a patient's mitral valve and used to secure a THV to the native leaflets of the mitral valve.

FIG. 19 shows an introducer sheath 400 inserted into the left ventricle of a patient's heart through a puncture 402. In particular implementations, the introducer sheath 400 is positioned so that it is not directly centered about the outflow side of the mitral valve, but rather is offset from the center. In particular, the introducer sheath 400 can be positioned so that it is on the exterior side of the space enclosed by chordae tendineae 412. It should be noted that in FIGS. 19-27, the chordae tendineae 412 of the left ventricle are only partially shown. It is to be understood, however, that the chordae tendineae 412 are respectively attached to each of the mitral valve leaflets and to the papillary muscles of the left ventricle. A surgeon can locate a distal tip 401 of the introducer sheath 400 near the outflow side of the mitral valve (e.g., within 1-10 millimeters).

Figure 20:
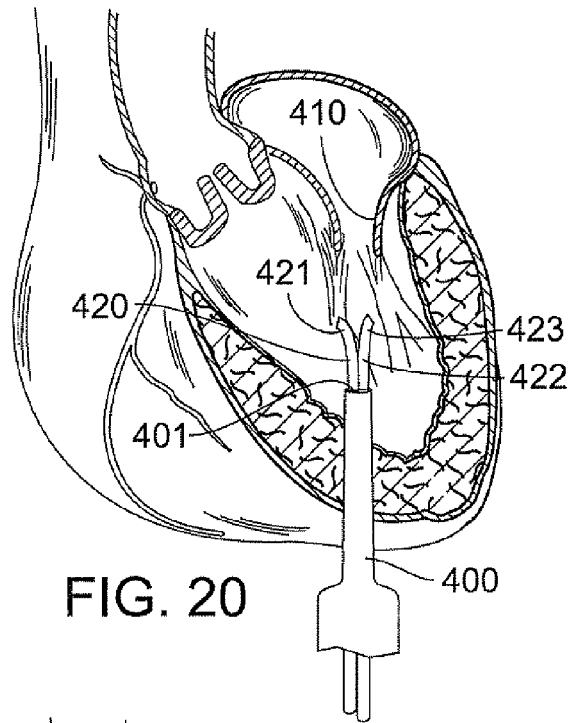

FIG. 20 shows a first catheter delivery sheath 420 and a second catheter delivery sheath 422 being advanced through the interior of the introducer sheath 400. The introducer sheath 400 can define two or more separate lumens through which the first and the second catheter delivery sheaths 420, 422 can be inserted or can define a single lumen sufficiently large to receive both the first and the second catheter delivery sheaths 420, 422. The first and second catheter delivery sheaths 420, 422 can be shaped so that they arc outwardly from each other when advanced out of the distal tip 401 of the introducer sheath 400. For example, in the illustrated embodiment, the first and second catheter delivery sheaths 420, 422 have end regions 421, 423 that arch about 90 degrees (or some other amount, such as between 45-90 degrees) when they are in their natural state. The amount of arching may vary from implementation to implementation but is desirably selected so that the tips of the end portions 421, 423 are in approximately the same plane. In other embodiments, the catheter delivery sheaths 420, 422 are not used as part of the support structure delivery procedure.

Figure 21:
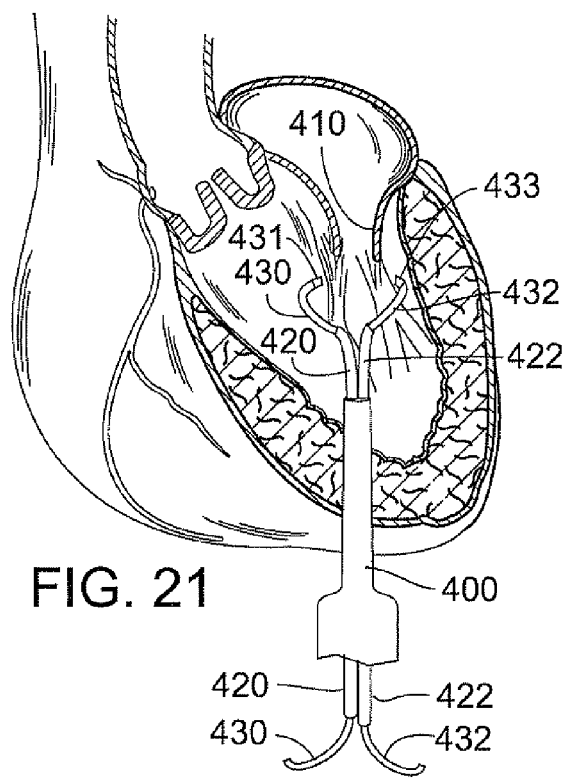

In FIG. 21, a first loop delivery catheter 430 is advanced through the interior of the first catheter delivery sheath 420 and extended substantially around the exterior of one half of the chordae tendineae (e.g., the medial half of the chordae tendineae). Similarly, a second loop deliver catheter 432 is advanced through the interior of the second catheter delivery sheath 422 and extended substantially around the exterior of the other half of the chordae tendineae (e.g., the lateral half of the chordae tendineae). The loop delivery catheters 430, 432 can be steerable catheters having end regions that can be selectively deformed or arched by an operator. Such steerable catheters are well known in the art. The loop delivery catheters 420, 432 can additionally be magnetic or have magnetic distal end portions. For example, in the illustrated embodiment, the first loop delivery catheter 430 has a magnetic distal end portion 431 with a first polarity, and the second loop delivery catheter 432 has a magnetic distal end portion 433 with a second polarity opposite the first polarity. As a result of their magnetization, the end portions 431, 433 are attracted to one another and will form a contiguous junction when in sufficient proximity to each other. Other mechanisms for engaging the end portions 431, 433 to one another are also possible (e.g., a hook mechanism, an adhesive, an enlarged diameter of one end portion, and other such mechanisms). When the end portions 431, 433 are engaged to one another, the first and the second loop delivery catheters 430, 432 form a single interior or lumen through which a support band material can be advanced. Furthermore, when the end portions 431, 433 are engaged to one another, the first and the second loop delivery catheters 430, 432 create a partial loop that circumscribes the chordae tendineae.

Figure 22:
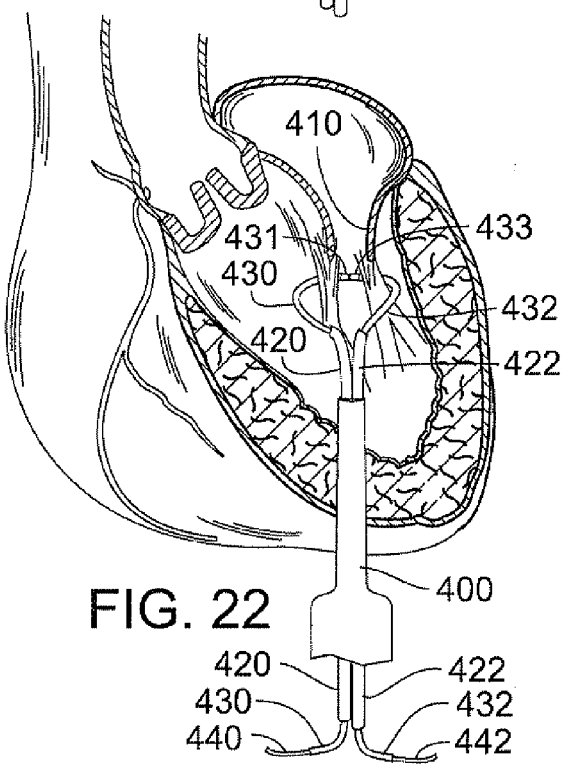

FIG. 22 shows the magnetic distal end portions 431, 433 after the first and second loop delivery catheters 430, 432 are arched around the chordae tendineae and after the distal end portions have been magnetically engaged to one another. In this configuration, a cord 440 of biocompatible material can be advanced through the interior of one of the loop delivery catheters 430, 432 and into the interior of the other one of the loop delivery catheters. As used herein, the term "cord" refers to a slender length of material that can be formed from a single strand, fiber, or filament, or can comprise multiple strands, fibers, or filaments. In one particular implementation, an end 442 of the cord 440 can be advanced from a proximal end of the first loop delivery catheter 430, through the interior of the first loop delivery catheter, through the junction formed by the distal end portions 431, 433, and through the interior of the second loop delivery catheter 432 until it appears on the proximate end of the second loop delivery catheter 432. In one particular embodiment, the cord 440 is a guidewire (e.g., a guidewire made of stainless steel or other suitable metal). The guidewire can then be attached to another cord of biocompatible material used to form the support band and pulled through the interior of the first and the second loop delivery catheters 430, 432, thereby positioning the cord of biocompatible material around the chordae tendineae in a partial loop. With the cord of biocompatible material delivered around the chordae tendineae, the first and second loop delivery catheters 430, 432 and the first and second catheter delivery sheaths 420, 422 can be retracted from the introducer sheath 400.

FIG. 23 shows a cord 443 of biocompatible material used to form the support band positioned around the chordae tendineae after the first and second loop delivery catheters 430, 432 and the first and second catheter delivery sheaths 430, 422 have been withdrawn. In FIG. 23, a sheath 450 is inserted over both ends of the cord 443 and over a first portion 444 and a second portion 446 of the cord 443, which run through the length of the sheath 450.

As shown in FIG. 24, a locking member 460 can be advanced over the first and second portions 444, 446 of the cord 443 and into the left ventricle. The locking member 460 can be advanced, for example, by a pusher tube 462 that pushes the locking member 460 over the portions 444, 446 of the cord 440. In one particular embodiment, the locking member 460 includes lumens or other openings configured to receive each of the two portions 444, 446 and permits movement along the portions 444, 446 in only a single direction. In certain other embodiments, the locking member 460 can be unlocked from the portions 444, 446 of the cord 440 and advanced in both directions along the cord 440. In the illustrated embodiment, the pusher tube 462 is further configured to sever the portions of the cord 440 that extend through a proximal side of the locking member 460, thereby releasing a support band 441 formed by the locking member 460 and the loop-shaped portion of the cord 443 from the pusher tube 462. As more fully shown in FIG. 25, the pusher tube 462 can further be formed of a shape memory material or include a deflection mechanism that allows the pusher tube to have an arched shape toward its distal end. On account of this arched shape, the pusher tube 462 can be used to better position the support band 441 formed by the loop-shaped portion of the cord 443 and the locking member 460 adjacent to the outflow side of the mitral valve such that the native leaflets of the mitral valve open into an interior of the support band 441.

As shown in FIG. 25, the sheath 450 can be withdrawn from the introducer sheath 400 once the locking member 460 and the pusher tube 462 are advanced into the left ventricle. A balloon catheter 470 can be advanced through the introducer sheath 400 and into the interior of the mitral valve 410 of the patient. Although not shown in the illustrated embodiment, the balloon catheter may be guided by a guidewire into the center of the mitral valve. Ultimately, and as seen in FIG. 25, a balloon portion 472 of the balloon catheter 470 around which a THV 480 is crimped can be located within the mitral annulus. Radiopaque markers or other imaging enhancers may be provided on the distal end of the introducer sheath 400 and the balloon catheter 470 to more accurately determine the position of the THV 480 relative to the native valve 410. In some embodiments, a surgeon can adjust the position of the THV 480 by actuating a steering or deflecting mechanism within the balloon catheter 470.

As also shown in FIG. 25, the locking member 460 and the pusher tube 462 can be positioned so as not to interfere with the balloon catheter 470. Furthermore, with the THV 480 properly positioned within the mitral valve 410, the pusher tube 462 can be used to position the support band 441 formed by the loop-shaped remaining portion of the cord 443 around the native valve leaflets of the mitral valve. Radiopaque markers or other suitable imaging enhancers can be provided on the pusher tube 462, the locking member 460, and/or the loop-portion of the cord to allow for the proper positioning of the support band 441 relative to the valve leaflets. With the THV 480 in its desired position, the balloon portion 472 of the balloon catheter 470 can be inflated, thereby expanding the THV 480 against the native valve leaflets and causing the leaflets to frictionally engage the interior surface of the support band 441. This expansion secures the THV 480 to the native valve leaflets. In other words, the expansion pinches the native leaflets of the mitral valve between the support band 441 and the THV 480, and thereby secures the THV within the annulus of the mitral valve.

As shown in FIG. 26, with the THV 480 secured against the native mitral valve leaflets and the support band 441, the balloon portion 472 of the balloon catheter 470 can be deflated and the balloon catheter withdrawn from the introducer sheath 400. The pusher tube 462 can then be disengaged from the loop 441. For example, the pusher tube 462 can comprise a cutting element at its distal end that can be activated by the surgeon from the proximal end. An example of one suitable cutting element is shown below with respect to FIG. 39. Alternatively, a separate cutting device (e.g., a cutting catheter or catheter having a controllable cutting element) can be inserted through the introducer sheath 400 and used to cut the portions of the cord 443 that extend through the proximal side of the locking member 460 and do not form part of the support band 441.

FIG. 27 shows the THV 480 secured within the native mitral valve after the support band 441 has been released from the pusher tube 462 and the pusher tube has been retracted from the introducer sheath 400. It should be noted that the THV 480 can take a variety of different forms and may comprise an expandable stent portion that supports a valve structure. The stent portion desirably has sufficient radial strength to hold the valve at the treatment site and to securely engage the support band 441.

It will be understood by those of ordinary skill in the art that the above-described loop deployment technique can be modified in a number of manners without departing from the disclosed technology. For example, in some embodiments, the THV is delivered and expanded into the mitral valve before the support band is delivered to the left ventricle. In these embodiments, the THV can be temporarily secured within the mitral valve. For example, the THV can be temporarily secured to the mitral valve using one or more anchoring members on the exterior of the THV (e.g., anchoring members having a main body and one or more hook-shaped or umbrella-shaped barbs). The THV can also be temporarily secured within the mitral valve through the use of one or more spring-loaded clamps, rivets, clasps, or other such fastening mechanisms. With the THV temporarily secured, the support band can be delivered around the native leaflets as described above and the diameter of the support band reduced until a desired frictional fit is created between the support band, the leaflets, and the THV. Any of the locking members described herein that allow the diameter of the support band to be adjusted can be used to achieve the desired diameter.

Figure 28:
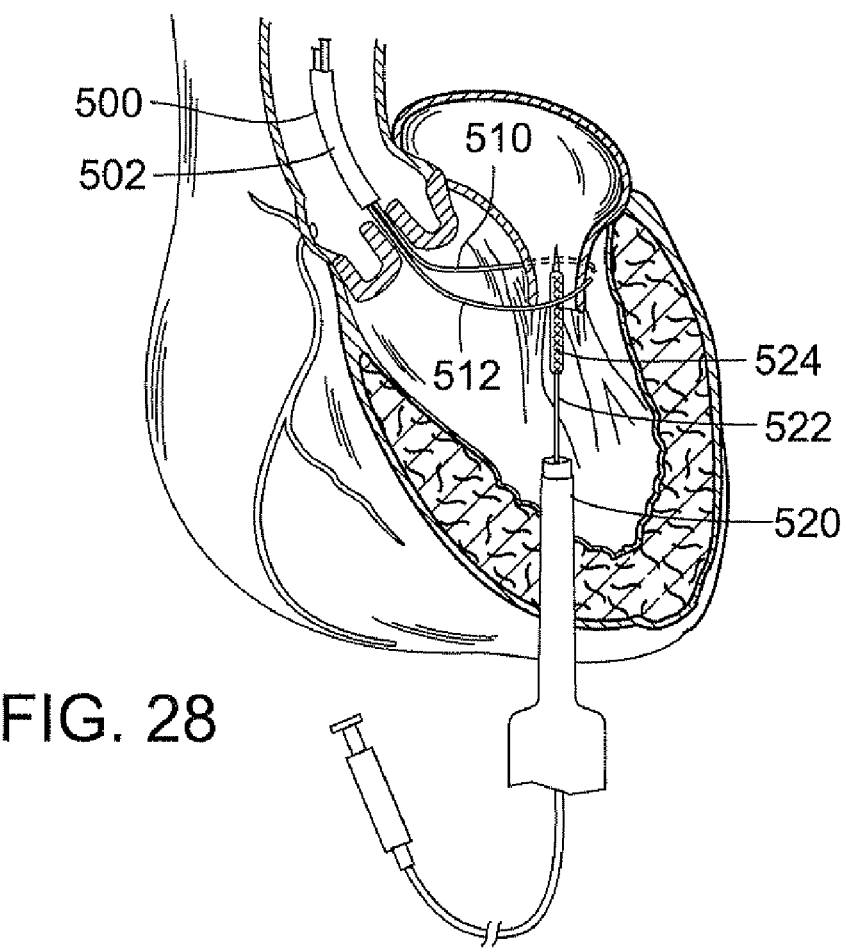
FIG. 28 is a cross-sectional view of a patient's heart illustrating how an exemplary support band as in FIGS. 19-27 can be deployed through the aortic arch.

Further, although the delivery method shown in FIGS. 19-27 uses a transapical approach, a delivery system adapted for introduction through the patient's aortic arch can alternatively be used. FIG. 28 shows an example of such a delivery system 500. In particular, FIG. 28 shows the delivery system 500 after a delivery catheter has been advanced through the aortic arch to a position adjacent the aortic valve and as a first loop deliver catheter 510 and a second loop deliver catheter 512 are deployed through the distal end of a delivery catheter 502. As with the procedure described above, the first and second loop delivery catheters 510, 512 can be steerable and comprise magnetic distal end portions that allow the catheters 510, 512 to engage one another on a distal side of the chordae tendineae, thereby forming a delivery lumen through which biocompatible material for the support band or loop can be deployed. Also shown in FIG. 28 is an introducer sheath 520 and a balloon delivery catheter 522 for deploying a THV 524. Besides the adaptations for aortic delivery, the delivery procedure can otherwise be substantially similar or identical to the procedure shown in FIGS. 19-27.

Still other delivery variations are possible. For instance, the support band may be formed of a shape-memory material that assumes a C-shape when not acted on by any external forces. The support band can be further configured such that one end of the C-shaped member is hollow and has a slightly larger diameter than the opposite end. To deliver the C-shaped support band, the support band can be stretched into a linear form and advanced through a delivery catheter (e.g., using a pusher element). In particular, the distal end of the delivery catheter can be positioned adjacent the chordae tendineae such that when the support band is advanced out of the distal end, it wraps around the chordae tendineae. After the support band is deployed from the distal end of the delivery catheter, a clamping device that is designed to engage the C-shaped support band and urge the ends of the support band together can be inserted into the heart (e.g., through the delivery catheter, the introducer sheath, or through a separate catheter). The clamping device can be used to urge one end of the support band into the hollow opposite end of the band. The ends can be crimped so that the support band forms a ring-shaped support band (e.g., using the clamping device or other device). In other embodiments, the hollow end of the support band can comprise a shoulder that engages an angled collar on the other end of the support band when the ends are urged together, thereby form a snap-fit connection. With the ends of the support band secured to one another, the support band can be positioned around the native leaflets of the mitral valve (e.g., using the clamping device or other positioning device) as a balloon catheter delivers a THV. Upon expansion, the THV will pinch the native valve leaflets between the outer surface of the THV and the interior surface of the support band, thereby securing the THV within the mitral valve.

In still another embodiment, the support band includes one or more clamping or fastening devices that can be used to clamp or fasten the support band to the native leaflets of the mitral leaflets. For example, the clamping or fastening devices can comprise spring-loaded clamps, anchoring members having one or more hook or umbrella-shaped barbs, clasps, or other such clamping or fastening mechanisms. In this embodiment, the support band still has a substantially fixed diameter such that when the THV is expanded into the interior of the mitral valve, the THV causes the native valve leaflets to be pinched against the interior surface of the support band, thereby securing the THV within the mitral valve. In still other embodiments, the THV itself can include one or more clamping or fastening devices designed to clamp or fasten the THV to the native leaflets of the mitral valve (e.g., any of the clamping or fastening mechanisms described above). In this embodiment, the THV can be secured directly to the native leaflets without the use of a support band or other support structure.

FIG. 29 shows one exemplary embodiment of a locking member that can be used for locking member 460 shown in FIGS. 19-27. In particular, FIG. 29 shows locking member 600, which can be a clamp, such as an adjustable, C-shaped clamp with interlocking teeth around a portion of the clamp. The locking member 600 has two arms 610, 612, each formed with interlocking teeth 620, 622. Interlocking teeth 620, 622 are configured to lock the clamp in one or more positions of varying circumference when pressure is applied to the two arms 610, 612 and pushes the arms together. Referring to FIG. 23, the cord portions (such as portions 446, 446) can be inserted into the interior 630 of the locking member 600. The arms 610, 612 can be pushed together and tightened so that the portions 444, 446 are secured in place (e.g., using a clamping device inserted into the left ventricle through the introducer sheath or using the pusher tube 462 modified to include a clamping mechanism). The interior 630 can additionally have grooves to increase the friction and decrease the slippage between the locking member 600 and the portions of the cord secured therein.

Figure 32:
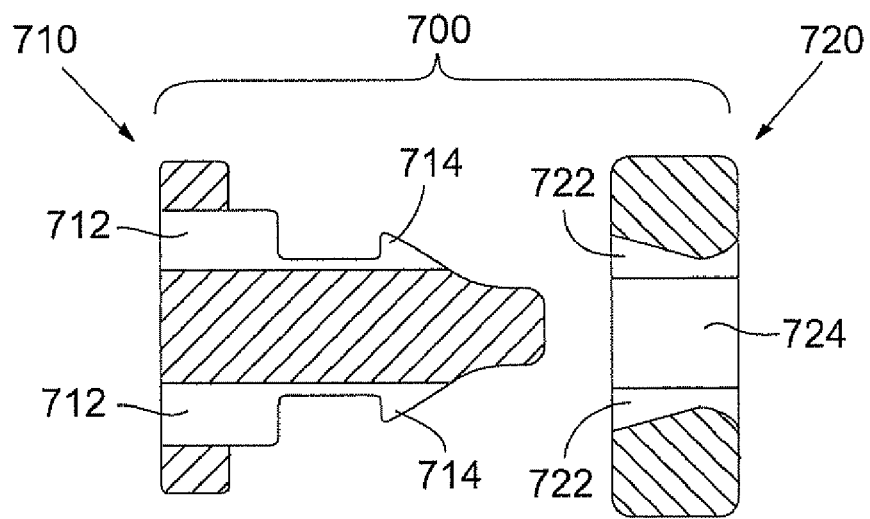
FIG. 32 is a cross-sectional side view of the exemplary locking member of FIG. 30.

FIGS. 30-37 depict another exemplary embodiment of a locking member that can be used for locking member 460 shown in FIGS. 19-27. In particular, FIGS. 30-37 show an adjustable locking member 700, which can be attached to two portions of a cord, thereby forming the support band. As best seen in FIGS. 30 and 32, the adjustable locking member 700 comprises a tapered, plastic pin 710 that fits into a tapered, plastic snap ring 720. When pin 710 and ring 720 are locked together, the adjustable locking member 700 is prevented from moving relative to the portions of the cord that are captured within the adjustable locking member 700 (e.g., cord portions 702, 704 in FIG. 30).

FIG. 31 illustrates an exemplary pusher tube (or adjustment catheter) 730 that can be used to introduce, position, and lock the adjustable locking member 700 in a desired position. The exemplary pusher tube 730 in the illustrated configuration has a fork member 732, an unlocking push member 734 that is extendable through the fork member 732, and a locking push member 736 that is extendable over the unlocking push member 734. Fork member 732 is configured so that it can move the adjustable locking member 700 over the cord portions to which it is connected. In particular, fork member 732 can engage the adjustable locking member 700 when it is positioned along the cord portions (but not yet in a locked position) such that by moving the pusher tube 730 in one direction along the length of the cord portions, adjustable locking member 700 is also moved. By moving the adjustable locking member 700 in this manner, the effective diameter of the support band formed by the cord and the adjustable locking member 700 can be modified.

Push members 734, 736 are slidably movable relative to each other and the fork member 732 to effect locking and unlocking of the adjustable locking member 700, as further described below. The unlocking push member 734 unlocks the adjustable locking member 700 from the locked position and the locking push member 736 locks the adjustable locking member 700 from the unlocked position.

FIG. 32 depicts the adjustable locking member 700, according to one embodiment, in more detail. The pin 710 comprises pin slots or holes 712 (which accept the cord portions) and locking members or flanges 714 (which extend outward to secure the pin to the ring in a locked position). Ring 720 comprises ring slots or holes 722 (which accepts the cord portions) and pin receiving hole 724 (which receives the pin to secure the pin to the ring in a locked position). The locking members 714 are deformable to allow the pin member to be inserted throughout ring member and form a snap-fit connection sufficient to hold the ring member on the pin member.

Figure 33:
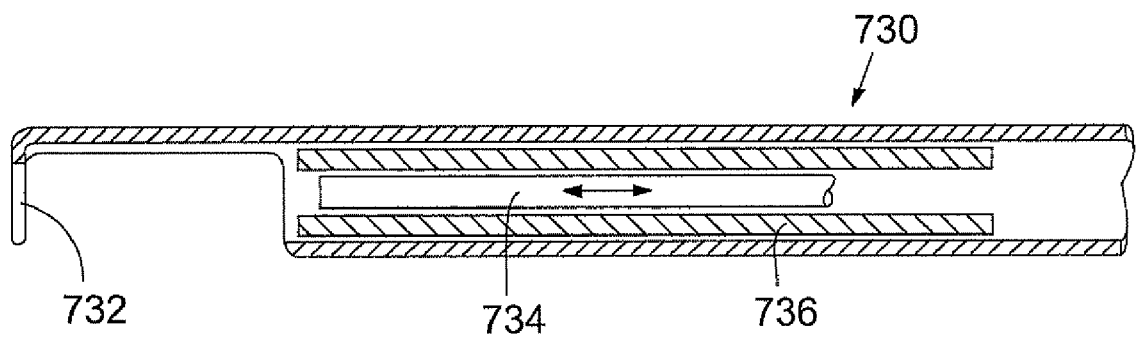
FIG. 33 is a cross-sectional side view of the exemplary adjustment tool of FIG. 31.

FIGS. 33-37 depict the relationship between the adjustable locking member 700 and the pusher tube 730, according to one embodiment, and their functions relative to one another. As discussed above, the pusher tube 730 comprises fork member 732, unlocking push member 734, and locking push member 736. FIG. 33 shows the pusher tube 730 in more detail. Both the unlocking push member 734 and the locking push member 736 are slidably movable within the pusher tube 730 along the longitudinal direction identified by the arrows shown in FIG. 33. The unlocking push member 734 is desirably a solid member that is sized to fit within the locking push member 736, which is desirably cylindrical with a longitudinally extending hollow section or lumen for receiving the unlocking push member 734.

Figure 34:
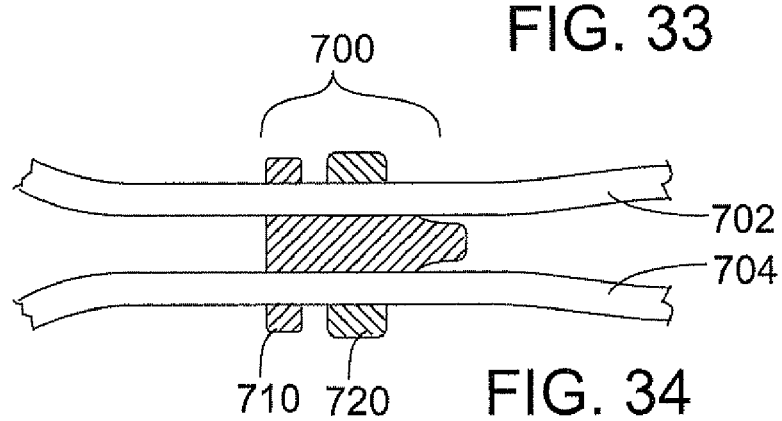
FIGS. 34-37 are cross-sectional views illustrating how the exemplary adjustment tool of FIG. 31 can be used to adjust, lock, and unlock the exemplary locking member of FIG. 30.

FIG. 34 shows the adjustable locking member 700 with the pin 710 and the ring 720 locked together. In the locked position, the cord portions 702, 704 pass inside the ring 720 and around the pin 710 (through the ring holes and pin holes) and are captured between these two components. The cord portions 702, 704 are held in place relative to each other, and the pin 710 and the ring 720 are held in place relative to the cord portions 702, 704 by the friction created at the surface interfaces.

Figure 35:
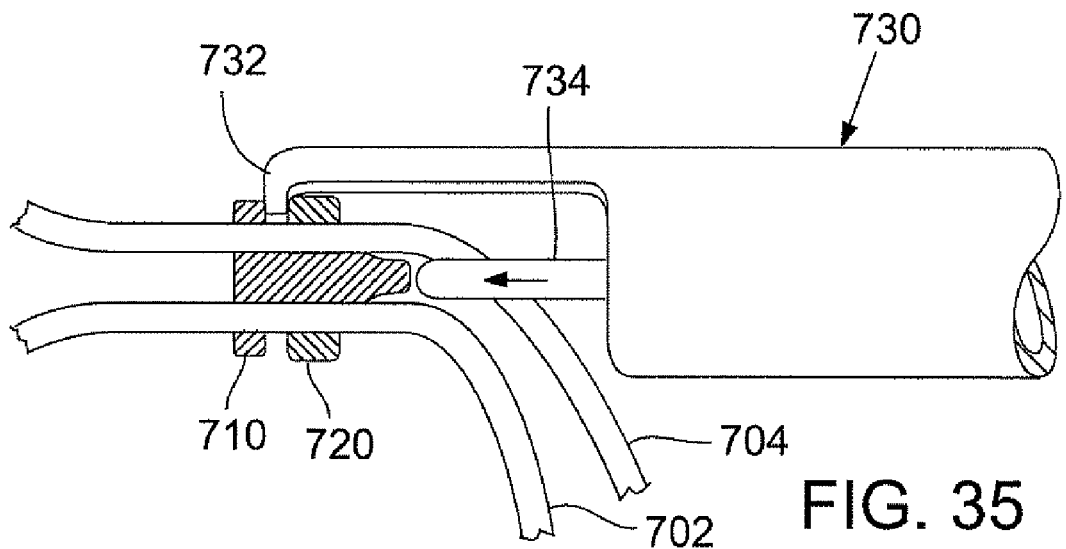
Figure 36:
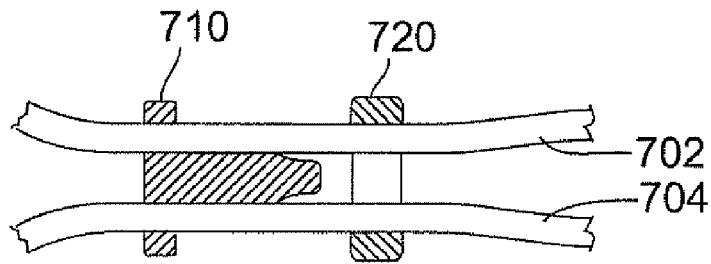

Referring to FIGS. 35 and 36, to unlock the adjustable locking member 700, the fork member 732 is inserted between the pin 710 and the ring 720, and the unlocking push member 734 is extended from the pusher tube 730 to push the pin 710 and the ring 720 apart. The fork member 732 holds the ring 720 in place, while the unlocking push member 734 applies longitudinal pressure against the tip of the pin 710, forcing it out of the ring 720. The unlocking push member 734 is desirably sized so that it can fit at least partially through the pin receiving hole 724 to assist in unlocking the pin 710 and the ring 720 from one another. Once the pin 710 and the ring 720 are separated, the adjustable locking member 700 can be moved relative to the cord portions 702, 704 in order to adjust the diameter of the support band formed by the cord portions 702, 704.

Figure 37:
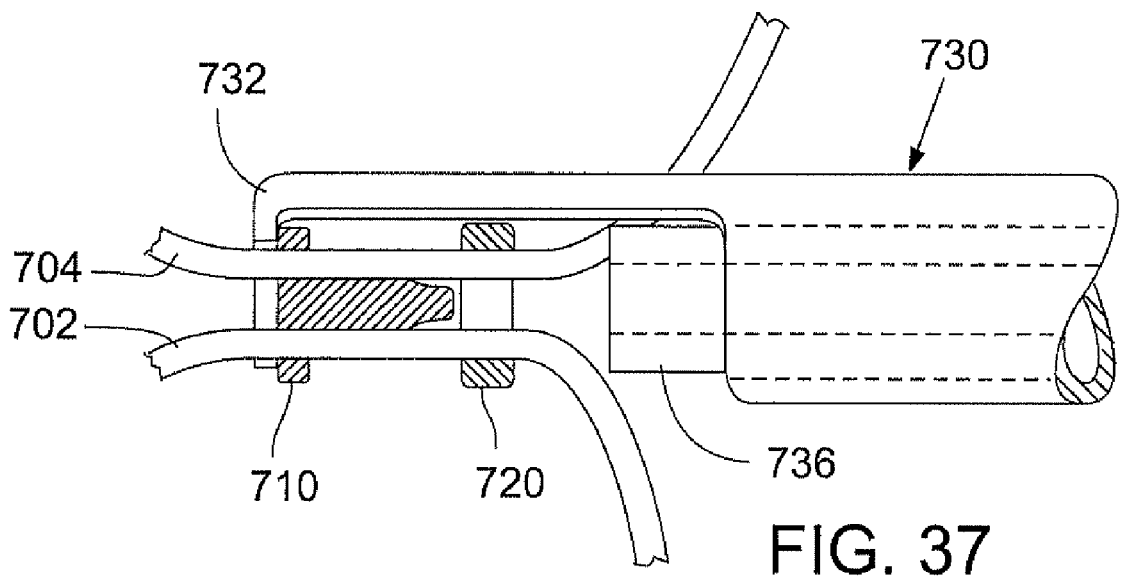

Referring to FIG. 37, the manner in which the pusher tube 730 can be used to secure the pin 710 and the ring 720 together is shown. The fork member 732 is placed at the far (distal) end of the pin 710 and the locking push member 736 is extended from the pusher tube 730. The locking push member 736 is configured with a cylindrical surface that is sized to mate with the area of the ring 720 that surrounds the pin receiving hole. While the fork member 732 holds the pin 710 in place, the locking push member 736 forces the ring 720 onto the pin 710 and locks the pin and the ring together. Once the adjustable locking member 700 is locked, the frictional engagement of the adjustable locking member with the cord portions maintains the position of the adjustable locking member relative to the cord portions 702, 704. The three-point connection system described above permits a surgeon to perform fine adjustments of the diameter of the support band around the chordae tendineae and around the outflow side of the native leaflets of the mitral valve.

Figure 38:
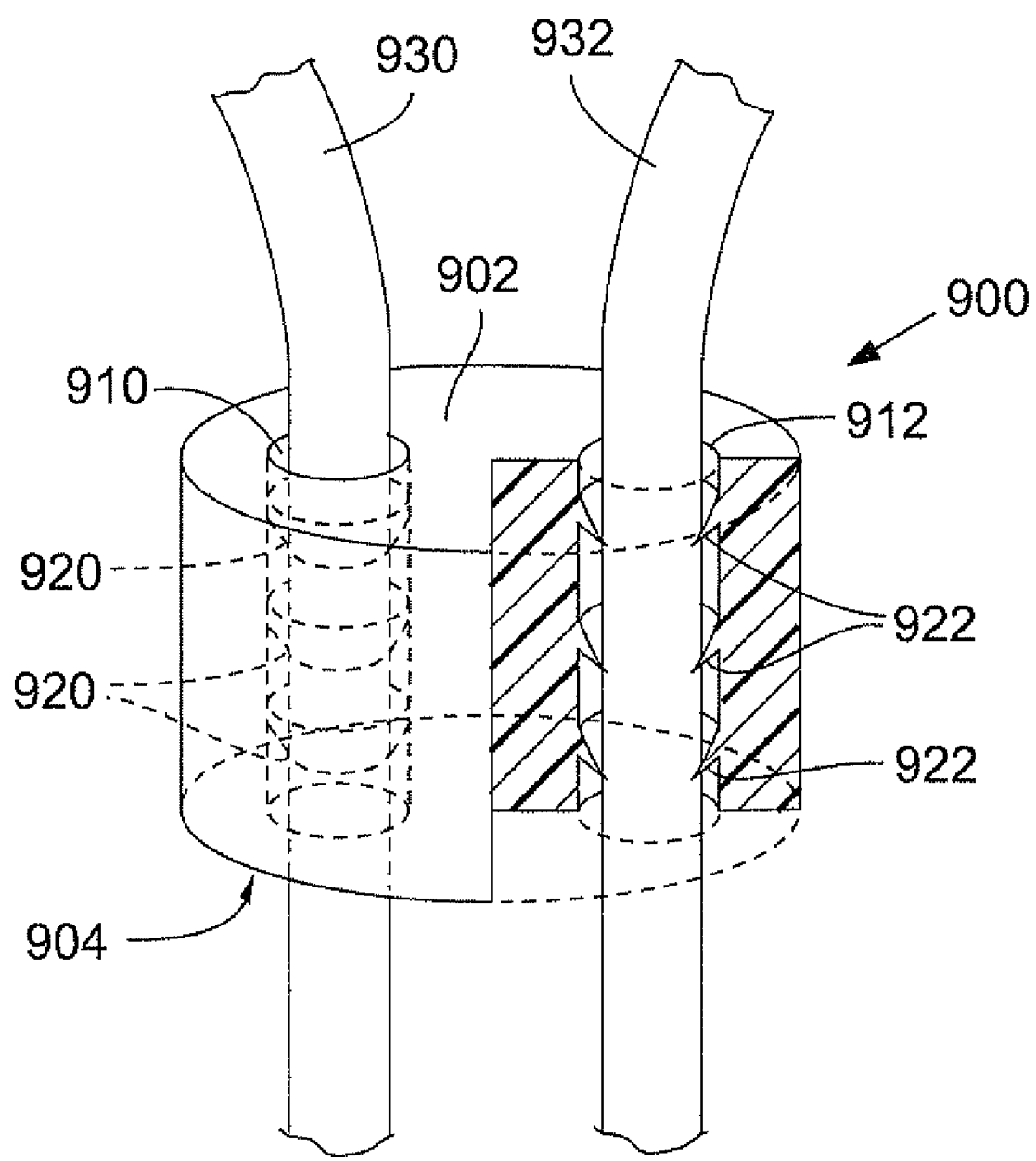
FIG. 38 is a cross-sectional perspective view of another exemplary locking member that can be used to secure portions of a cord of support band material to one another and thereby form a loop.
Figure 39:
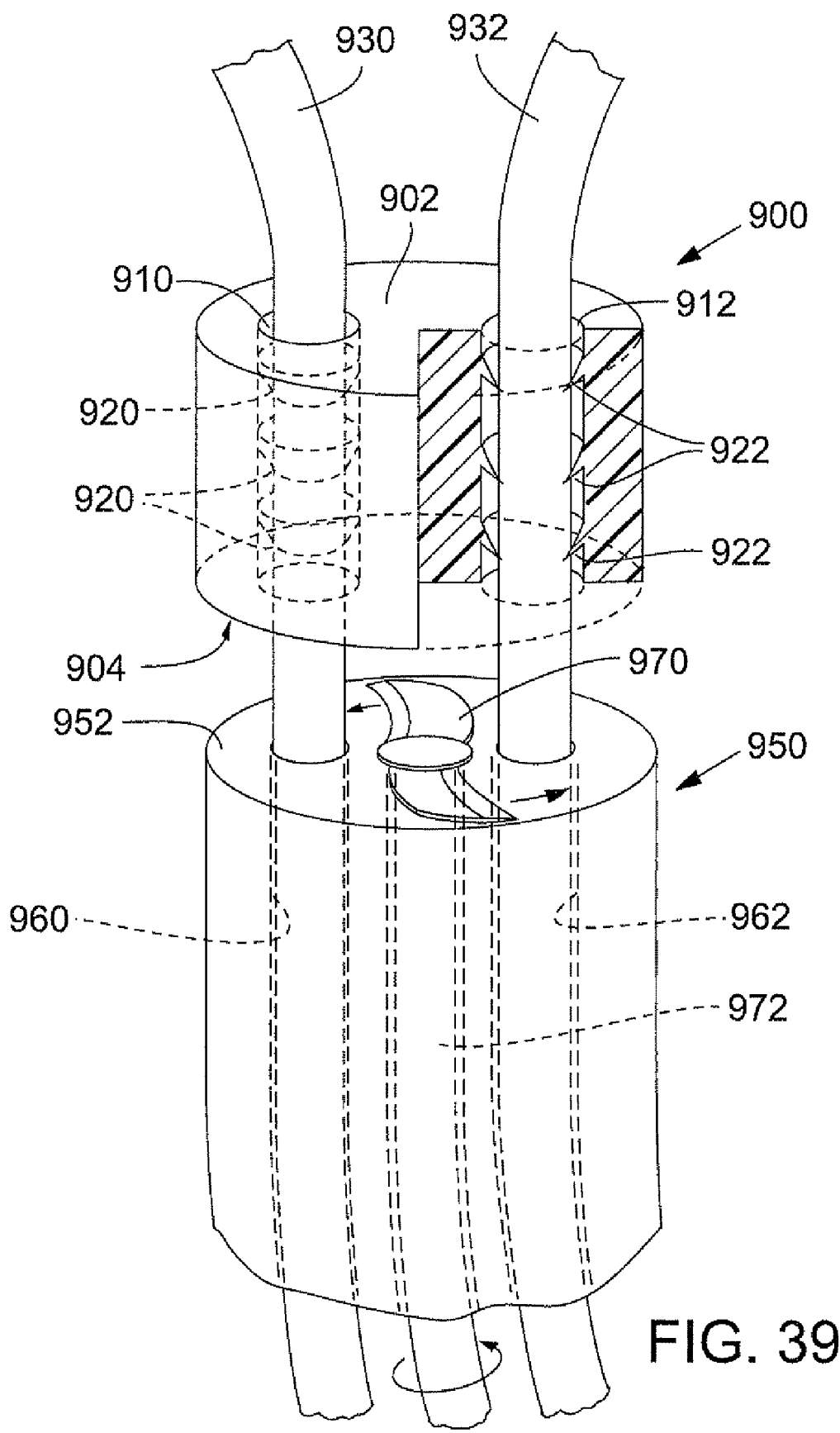
FIG. 39 is a cross-sectional perspective view of an exemplary pusher tube that can be used in connection with the exemplary locking member of FIG. 38.

FIGS. 38-39 depict another exemplary embodiment of a locking member that can be used for locking member 460 shown in FIGS. 19-27. In particular, FIG. 38 shows an adjustable locking member 900 having a generally cylindrical body with two lumens (or apertures) 910, 912 formed therein that extend from a top surface 902 to a bottom surface 904 of the body. In the illustrated embodiment, and as best seen in the cut-away portion of FIG. 38 showing the lumen 912, the interior of the lumens 910, 912 comprises a plurality of teeth (or collars) 920, 922 that are angled toward the bottom surface 904. The teeth 920 can have some flexibility and be formed to allow a cord portion, such as cord portion 930 or cord portion 932, to slide through the lumens 910, 912 in a first direction, but not in an opposite second direction. In other words, the teeth 920, 922 of the adjustable locking member 900 allow for one-way movement of the locking member 900 along the cord portions 930, 932. In this way, the adjustable locking member 900 can be used to securely form the support band and allows for the diameter of the support band to be adjusted to its desired size.

FIG. 39 shows an exemplary embodiment of a pusher tube 950 that can be used with the adjustable locking member 900 (e.g., the pusher tube 950 can be used as the pusher tube 462 shown in FIGS. 19-27). The exemplary pusher tube 950 includes lumens 960, 962 through which the cord portions 930, 932 can extend. In a particular embodiment, the lumens 960, 962 have a sufficiently large diameter and a smooth interior that allows the cord portions 930, 932 to more easily slide therethrough. In the illustrated embodiment, the pusher tube 950 further includes a rotatable blade 970 at its distal end 902. The rotatable blade 970 can be rotatable about a central axis of the pusher tube 950 and connected to an interior rod member 972 that extends through a central lumen of the pusher tube 950. A handle (not shown) can be attached to the interior rod member 972 at its proximal end and allow for an operator to manually rotate the rotatable blade 970 in order to sever the pusher tube 950 from the adjustable locking member 900.

Other methods of delivering a support band and THV to the mitral valve or any other heart valve are also possible. For example, in certain embodiments, the support band and the THV are delivered surgically to the desired heart valve (e.g., in an open-heart surgical procedure). Furthermore, in certain embodiments in which the support band and THV are delivered surgically, non-compressible THVs are used.

Having illustrated and described the principles of the disclosed technology, it will be apparent to those skilled in the art that the disclosed embodiments can be modified in arrangement and detail without departing from such principles. In view of the many possible embodiments to which the principles of the disclosed technologies can be applied, it should be recognized that the illustrated embodiments are only preferred examples of the technologies and should not be taken as limiting the scope of the invention. Rather, the scope of the invention is defined by the following claims and their equivalents. We therefore claim all that comes within the scope and spirit of these claims.

What is claimed is:

1. A method of treating aortic insufficiency, comprising:
   delivering a support structure to an outflow side of an aortic valve of a patient, the support structure comprising an annular body defining an interior;
   positioning the annular body around leaflets of the aortic valve such that the leaflets of the aortic valve are located within the interior of the annular body and the annular body circumscribes the leaflets of the aortic valve;
   after positioning the annular body around the leaflets of the aortic valve, delivering an expandable prosthetic heart valve to a vicinity of the aortic valve, the prosthetic heart valve being advanceable independently of the support structure;
   advancing the expandable prosthetic heart valve into the interior of the annular body while the annular body is maintained in a substantially fixed position relative to the aortic valve; and
   expanding the expandable prosthetic heart valve into contact with the leaflets of the aortic valve, thereby causing the leaflets of the aortic valve to be frictionally secured between an inner surface of the annular body and an outer surface of the prosthetic heart valve.

2. The method of claim 1, wherein the expandable prosthetic heart valve is delivered from an inflow side of the aortic valve.

3. The method of claim 1, wherein the expandable prosthetic heart valve is delivered from the outflow side of the aortic valve.

4. The method of claim 1, wherein the act of delivering the expandable prosthetic heart valve comprises delivering the prosthetic heart valve through a left ventricle of the patient's heart.

5. The method of claim 1, wherein the act of delivering the expandable prosthetic heart valve comprises delivering the prosthetic heart valve through the patient's aorta.

6. The method of claim 1, wherein the support structure is a support stent, and wherein the act of delivering the support structure comprises:
   advancing a first catheter through an aortic arch of the patient so that a distal end of the first catheter is near the aortic valve of the patient, the first catheter at least partially enclosing a stent-delivery catheter, an inner catheter, and the support stent in a compressed state; and
   advancing the stent-delivery catheter and the inner catheter through the first catheter, thereby causing the support stent to be deployed from the distal end of the first catheter and to expand into an uncompressed state.

7. The method of claim 1, wherein the act of delivering the support structure comprises guiding the support structure to the outflow side of the aortic valve and into a desired orientation, wherein the desired orientation aligns peaks of the support structure with either the tips or the commissures of the leaflets.

8. The method of claim 1, further comprising disconnecting the support structure from at least a delivery catheter once the leaflets of the aortic valve are frictionally secured between the inner surface of the annular body and the outer surface of the prosthetic heart valve.

9. The method of claim 8, wherein the disconnecting comprises retracting an inner catheter relative to a stent-delivery catheter, thereby retracting inner prongs coupled to the inner catheter from corresponding apertures in retaining arms of the support structure.

10. The method of claim 8, wherein the disconnecting comprises cutting through material used to form the support structure.

11. The method of claim 1, wherein the act of expanding the expandable prosthetic heart valve comprises inflating a balloon of a balloon catheter, the expandable prosthetic heart valve being disposed around the balloon of the balloon catheter.

* * * * *